US010783221B1

(12) United States Patent
Dowling et al.

(10) Patent No.: US 10,783,221 B1
(45) Date of Patent: *Sep. 22, 2020

(54) AUTOMATED HEALTHCARE CASH ACCOUNT RECONCILIATION SYSTEM

(71) Applicant: The PNC Financial Services Group, Inc., Pittsburgh, PA (US)

(72) Inventors: Margaret C. Dowling, Philadelphia, PA (US); Laurie Olender, Rocky River, OH (US); Doreen Franks, Pittsburgh, PA (US); Loretta Lehman, Pittsburgh, PA (US); Heather Henkel, Pittsburgh, PA (US); Patrick Gallagher, Pittsburgh, PA (US); Thomas Coast, New Brighton, PA (US); Bryan Jeffers, Pittsburgh, PA (US); Matthew Feeney, Pittsburgh, PA (US)

(73) Assignee: The PNC Financial Services Group, Inc., Pittsburgh, PA (US)

( * ) Notice: Subject to any disclaimer, the term of this patent is extended or adjusted under 35 U.S.C. 154(b) by 1127 days.

This patent is subject to a terminal disclaimer.

(21) Appl. No.: 14/603,721

(22) Filed: Jan. 23, 2015

Related U.S. Application Data

(60) Provisional application No. 61/931,110, filed on Jan. 24, 2014.

(51) Int. Cl.
*G06F 19/00* (2018.01)

(52) U.S. Cl.
CPC ................................. *G06F 19/328* (2013.01)

(58) Field of Classification Search
CPC ........ G06Q 40/08; G06Q 40/12; G06Q 40/00; G06Q 20/04; G06Q 20/10; G06Q 20/102; G06Q 20/14; G06Q 10/10; G06F 19/328
USPC ........................................................ 705/2–3
See application file for complete search history.

(56) References Cited

U.S. PATENT DOCUMENTS

| | | | |
|---|---|---|---|
| 8,364,688 B1 * | 1/2013 | Thomas ................ | G06Q 10/10 707/758 |
| 2007/0265887 A1 * | 11/2007 | McLaughlin .......... | G06Q 50/22 705/4 |
| 2008/0059223 A1 * | 3/2008 | Lu .......................... | G06Q 40/02 705/2 |
| 2008/0077438 A1 * | 3/2008 | Yanak .................... | G06Q 20/14 705/2 |

(Continued)

*Primary Examiner* — Joy Chng
(74) *Attorney, Agent, or Firm* — Buchanan Ingersoll & Rooney PC; Robert J. Pugh

(57) ABSTRACT

A system and method for reconciling a healthcare payment account includes receiving: (a) a first file that includes sorted and rebalanced explanation of benefits information from a healthcare payer, the first file generated by segregating comingled data for multiple healthcare providers or accounting systems; (b) a second file that includes payment information for a bank account of a healthcare provider; and, (c) a third file that includes accounting information from the healthcare provider; using reassociation and file splitting processes to match transactions of at least two files using rules based logic, and to calculate variances of transactions between at least two files; and, displaying at least one of variance via at least one GUI to facilitate reconciliation.

20 Claims, 25 Drawing Sheets

(56) References Cited

U.S. PATENT DOCUMENTS

2011/0258004 A1* 10/2011 Dean ............... G06Q 10/10
 705/4
2012/0130736 A1* 5/2012 Dunston ............ G06Q 50/22
 705/2

* cited by examiner

FIG. 7B

Manual Payment Reassociation

*Fields marked with * are required*

| | |
|---|---|
| Provider Orlandohealth Central Office: | Payer BCBStd Insurance Company: | Received Date: 01/16/2015 15:38:49 |

Payment Details

| | |
|---|---|
| Dollar Amount: $1,835.54 | Provider ID: 1209120002 | Payer ID: 120912100 |
| Deposit Date: 11/12/2014 00:00:00 | Provider Qualifier: XX | Payer Qualifier: FI |
| Originator Company Name: BCBStd | Trace ID / 22346EFT789SHAA | Payment Type: ACH |
| | Check Number: | |

Remittance Details

| Remittance ID | Remittance Amount | Trace / Check Number | Check Issue Date | Reassociation Status | Reassociation Status |
|---|---|---|---|---|---|
| 18103628 | $2,000.00 | 2236ACH6433HA13 | 09/18/2014 | Waiting For Reassociation | Manual Task |
| 18103561 | $2,500.11 | 2236ACH644REM14 | 11/14/2014 | Waiting For Reassociation | Manual Task |
| 18186656 | $473.71 | EFT111559 | 12/13/2012 | DISCARD | Pending |
| 18211388 | $835.54 | 346EFT789SHAA | 11/13/2014 | Waiting For Reassociation | Pending |
| 18211620 | $1,635.54 | A346EFT789SHAA | 11/13/2014 | Waiting For Reassociation | Pending |

```
ISA*00*          *00*          *ZZ*061118515  *01*043000096
*080913*1011*U*00401*000000979*0*P*>~
ST*835*40501~
BPR*X*0*C*ACH*CCP*01*694656321*DA*875439*158754397*1999999999*0
1*999986690*DA*98765*20080313~
TRN*1*6025*1587543978*847590324~
DTM*405*20080313~
N1*PR*Oxford Health Plans~
N3*225 Pioneer Stree~
N4*Bellevue*WA*98004~
CLP*7722357*4*14.73*0*0*HM*725932404007801*81*0~
NM1*62*2*PATIENT NAME****PC*A1893530~
SVC*HC>89175>90*114.73*0**1~
DTM*472*20071212~
CAS*OA*24*114.73~
SE*423*40500l~
IEA*1*000000979~
```

AUTOMATED HEALTHCARE CASH ACCOUNT RECONCILIATION SYSTEM

CROSS-REFERENCE TO RELATED APPLICATIONS

This patent application claims the benefit of, and priority to, U.S. Provisional Patent Application No. 61/931,110, filed on Jan. 24, 2014, which is incorporated by reference herein in its entirety.

FIELD OF THE DISCLOSURE

The present disclosure is generally directed towards a system and method for reconciling a healthcare provider financial record system based on accounting transactions posted to bank accounts, patient accounting or revenue cycle systems, and other systems used by the provider to facilitate accounts receivable or cash collections.

BACKGROUND

Healthcare providers have difficulty reconciling various revenue systems to the bank accounts. Amounts are posted at the patient account level in an accounts receivable system of a healthcare provider, while amounts are posted at the payment level on bank statements for the healthcare provider. Each payment may represent reimbursement for hundreds of individual patient accounts. Payments posted on the bank statement could represent a cash payment, an individual check, an Electronic Funds Transfer ("EFT") for payment of a medical claim from an insurance company, or a deposit ticket for cash or checks collected over the counter.

Problems arise when the various sources of revenue data are commingled into one financial data collection. For instance, cash payments and individual patient checks deposited via one deposit ticket make it difficult to reconcile total cash collected to the individual patient accounts posted on an accounts receivable system. Furthermore, information relating to payment of a medical claim by an insurance company may be received by a healthcare provider such that the information regarding a particular patient accounting system or provider entity is commingled with data for different patient accounting systems or provider entities.

In the Healthcare industry these problems are typically dealt with by using manually intensive data entry. According to some market research, most healthcare providers perform daily cash reconciliation using Excel® spreadsheets. The process typically requires an average of one or more full time employees per hospital or health system accounting entity. With manual data entry, there is the possibility for error, and delays in data entry may increase audit problems and financial risk.

Current reconciliation technology that has sought to alleviate these problems has not accomplished its goal. Many systems and methods still require much manual data entry and require costly installation of software at a healthcare provider's location. Furthermore, many of these systems are platform dependent, and can only be used with specific patient accounting systems. Thus, there is a need for a healthcare cash reconciliation system that is cost effective, system-agnostic, and solves the aforementioned problems.

SUMMARY OF THE DISCLOSURE

As disclosed herein, a hosted system includes a database in which method implemented by the system collects and compares banking information from a healthcare provider's financial institution(s) via Bank Administration Institute ("BAI") files or payment files in other data formats, information extracted from explanation of benefits files from a medical claims payer, such as an insurance company, that may be received by the hosted database via a bank and/or healthcare clearinghouse, and accounts receivable and general ledger information transmitted from a healthcare provider's systems. The system and method enables matching and comparison of the three sources of information by a user, and the user is able to access reports that highlight deposit variances for, among other things, reconciliation. The system and method enables a user to research and resolve payment variances, either by making corrections on an accounts receivable and/or general ledger system or by tracking missing payments or data files. The system and method also enables a user to use rules-based logic to identify and separate data from disparate patient accounting systems or provider entities to address the aforementioned problem of commingled data.

Various other objects, aspects and advantages of the present disclosure can be obtained from a study of the specification, the drawings, and the appended claims.

In exemplary embodiments, a method for reconciling a healthcare payment account comprises receiving, by a computing device having a processor, a display, and non-transitory computer readable medium, a first electronic file that comprises explanation of benefits information from a healthcare payer, receiving, by the computing device, a second electronic file that comprises payment information for a financial account of a healthcare provider, and receiving, by the computing device, a third electronic file that comprises accounting information from the healthcare provider.

The method includes calculating, by the computing device, a first variance that comprises a variance between the first electronic file and the second electronic file, calculating, by the computing device, a second variance that comprises a variance between the second electronic file and the third electronic file, calculating, by the computing device, a third variance that comprises a variance between the first electronic file and the third electronic file, and displaying, by the computing device on the display, at least one of the first variance, the second variance, and the third variance. The method includes reassociation and/or file splitting processes that are implemented through reassociation and/or file splitting modules of the system. These reassociation and/or file splitting processes enable calculating variances between data extracted from files comprising: 1) a healthcare provider's banking information; 2) a medical claims payer's explanation of benefits information; and, 3) a healthcare provider's accounts receivable and general ledger information so as to facilitate reconciliation of payments and remittances while: a) reducing, or eliminating, manual data entry; b) eliminating installation of costly platform-dependent software; and, c) enabling identification and separation of data from disparate patient accounting systems/provider entities.

In particular, the reassociation process enables: associating at least one provider with at least one payer; performing matching via TRN segment and Amount, Trace number, Transaction Date and Amount, and Amount only; performing the matching for an entire file and for each transaction; associating a remittance with a payment for reconciliation; and, displaying by the cash account reconciliation module at least at least one of the first variance, the second variance, and the third variance. The file splitting process enables: processing at least one of the first electronic file, the second electronic file, and the third electronic file such that at least one of the first electronic file, the second electronic file, and the third electronic file is split into a plurality of separate sub-files based on at least one of an accounting entity and an accounts receivable system; wherein at least one pre-defined data element within at least one of the first electronic file, the second electronic file, and the third electronic file is used to sort information within at least one of the first electronic file, the second electronic file, and the third electronic file; wherein the plurality of separate sub-files are subsequently rebalanced to a payment amount on at least one of the first electronic file, the second electronic file, and the third electronic file; and, wherein if a match is not determined, the at least one pre-defined data element is placed into an exception sub-file.

The system and method further generates reports displaying the results of the reassociation and file splitting processes, wherein graphical user interfaces ("GUIs") enable users to access data from databases of the system to manipulate reports, analyze variances, and coordinate reconciliation activities.

Advantages of the present disclosure include the ability to integrate standard bank data with healthcare specific transaction data to facilitate cash account reconciliation, the automatic collection of reconciliation data from banking and provider/client systems, and the ability to separate and balance data for different accounting entities and accounts receivable ("A/R") systems. Other advantages include automating the healthcare three-way matching process, identification and reporting of reconcilement variances, enabling users to enter data to reconcile reported variances, enabling users to export and save a final reconciliation report.

BRIEF DESCRIPTION OF THE DRAWINGS

Further possible embodiments are shown in the drawings. The present invention is explained in the following in greater detail as an example, with reference to exemplary embodiments depicted in drawings. In the drawings:

FIG. 7B illustrates an exemplary report generated by the manual explanation of benefit data matching process depicted in FIG. 6C, which presents payments that are possible matches for the selected remittance, in accordance with a preferred embodiment of the present disclosure;

FIG. 8B illustrates an exemplary report generated by the manual payment data matching process depicted in FIG. 6D, which presents remittances that are possible matches for the selected payment, in accordance with a preferred embodiment of the present disclosure;

FIG. 8C illustrates an exemplary report generated by the payment data matching process depicted in FIG. 6D, showing all payments meeting the search criteria selected, with their reassociation statuses, in a format suited for export to a general ledger or other accounting system, in accordance with a preferred embodiment of the present disclosure;

FIG. 9 illustrates information contained in an exemplary Direct 835 file format that may be used by the system and method, in accordance with a preferred embodiment of the present disclosure;

FIG. 10 illustrates a BPR segment contained in an exemplary Direct 835 file that may be used by the system and method, in accordance with a preferred embodiment of the present disclosure;

FIG. 11 illustrates a CLP segment contained in an exemplary Direct 835 file that may be used by the system and method, in accordance with a preferred embodiment of the present disclosure;

FIG. 12 illustrates exemplary patient account identification information that may be used by the system and method, in accordance with a preferred embodiment of the present disclosure;

DETAILED DESCRIPTION

The followings terms and definitions are used herein:

Payer—An insurance company or other payment entity that pays a healthcare claim that has been submitted for medical services provided to a patient.

Healthcare Provider—A healthcare provider entity that renders medical services to patients. This may be for example a hospital, physician, or other entity.

Current Procedural Terminology ("CPT")—A medical code set and maintained by the American Medical Association that describes medical, surgical, and diagnostic services, and is designed to convey uniform information about medical services and procedures among physicians, coders, patients, accreditation organizations, and payers for administrative, financial, and analytical purposes.

Automated Clearinghouse/Electronic Funds Transfer ("ACH/EFT")—An electronic payment transmitted via the banking system.

Bank Administration Institute ("BAI") File—A banking industry format for transmitting electronic lockbox or bank statement information (lockbox checks, or balances and individual bank statement transactions). A lockbox is a service offered by financial institutions to organizations that simplifies collection and processing of account receivables by having those organizations' customers' payments transmitted directly to a data storage location accessible by the financial institution. This can be done physically or electronically.

Explanation of Benefits ("EOB")—A paper document that explains how payment for a medical claim a patient of the healthcare provider was calculated by the healthcare payer. This is usually mailed with a check payment (or without a check if payment is denied). This may also be referred to as a "remittance" or "remit."

Direct 835 file—An industry format for transmitting EOB information electronically. This may also be referred to as an electronic remittance or Electronic Remittance Advice ("ERA"). This may also be referred to as a "manufactured" 835.

Financial Information ("BPR")—A single payment from a payer to a provider entity, as represented in the Direct 835 file. The BPR represents the total of payments made for individual patients (CLPs) within the Direct 835 file transaction, and it should match one or more checks or electronic funds transfers transmitted to the bank account of the provider entity.

Patient Level Payment Information ("CLP")—Claim payment information, or information contained within the Direct 835 file about payments made for individual patients and their specific claims.

Provider Level Balance ("PLB")—An adjustment to a payment taken by the payer that is not applied to a patient account displayed on the current EOB or Direct 835 file. Common PLBs include "recoupment" of a prior payment due to a claim being audited or an interest payment because a claim is being paid late. Cash reconciliation variances are often caused by PLBs.

Exemplary Network and System Implementations

Figure 1:
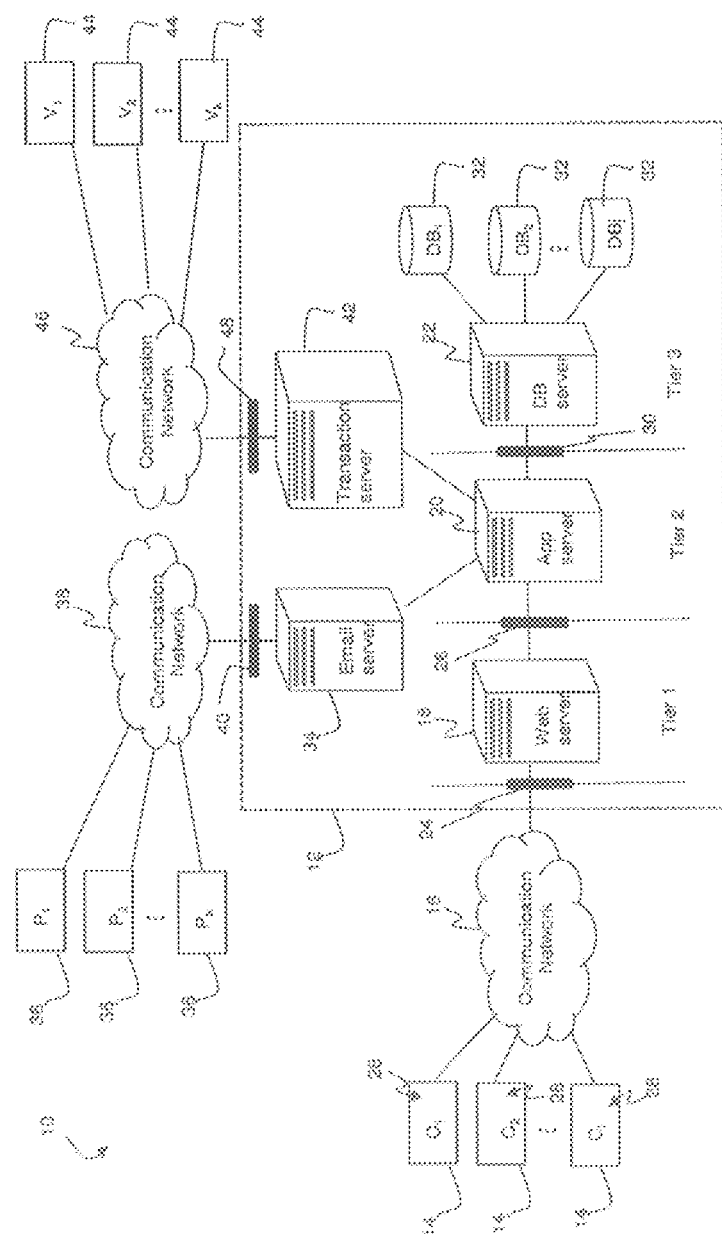
FIG. 1 illustrates exemplary network architecture for various exemplary embodiments of the present disclosure.
Figure 2:
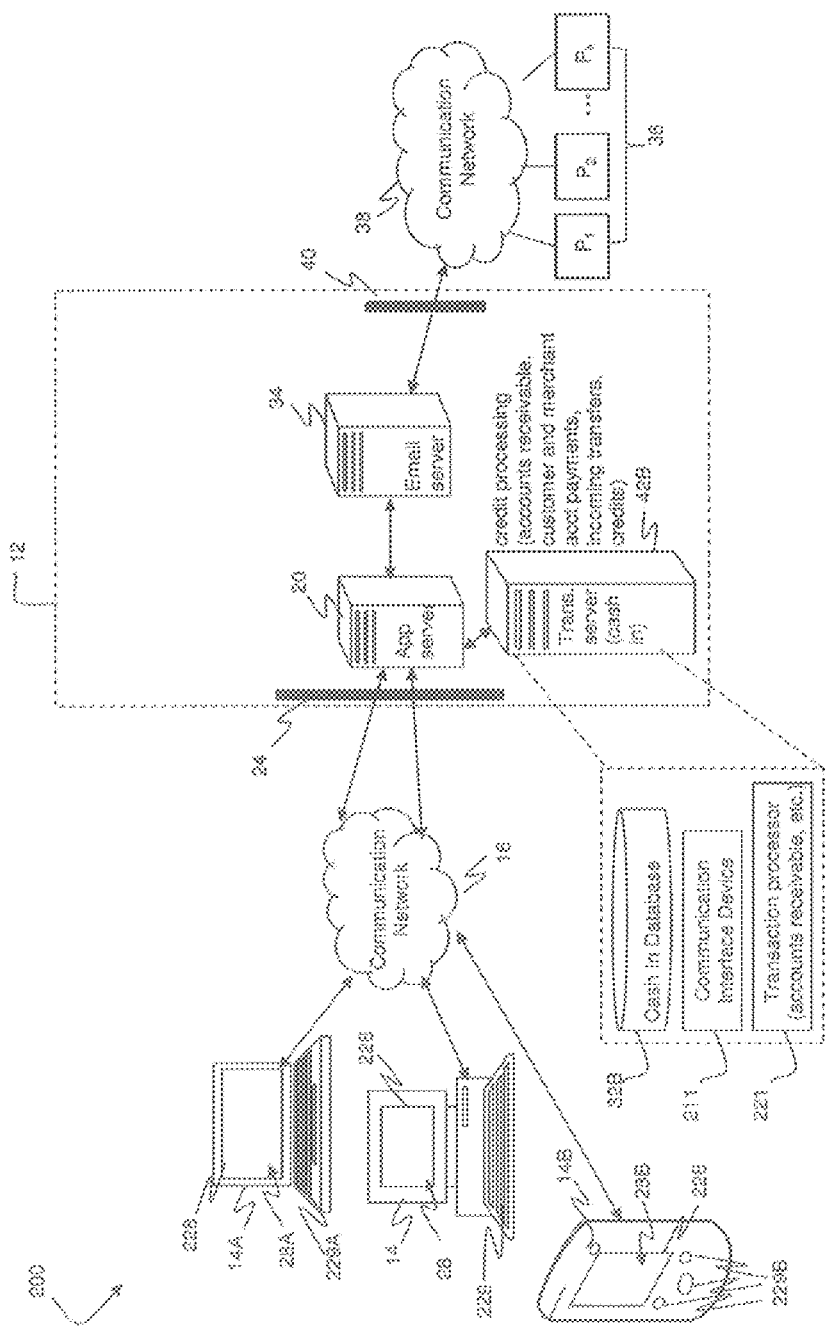
FIG. 2 illustrates an exemplary system in which reconciliation of a healthcare account may be performed, in accordance with a preferred embodiment of the present disclosure.
Figure 3:
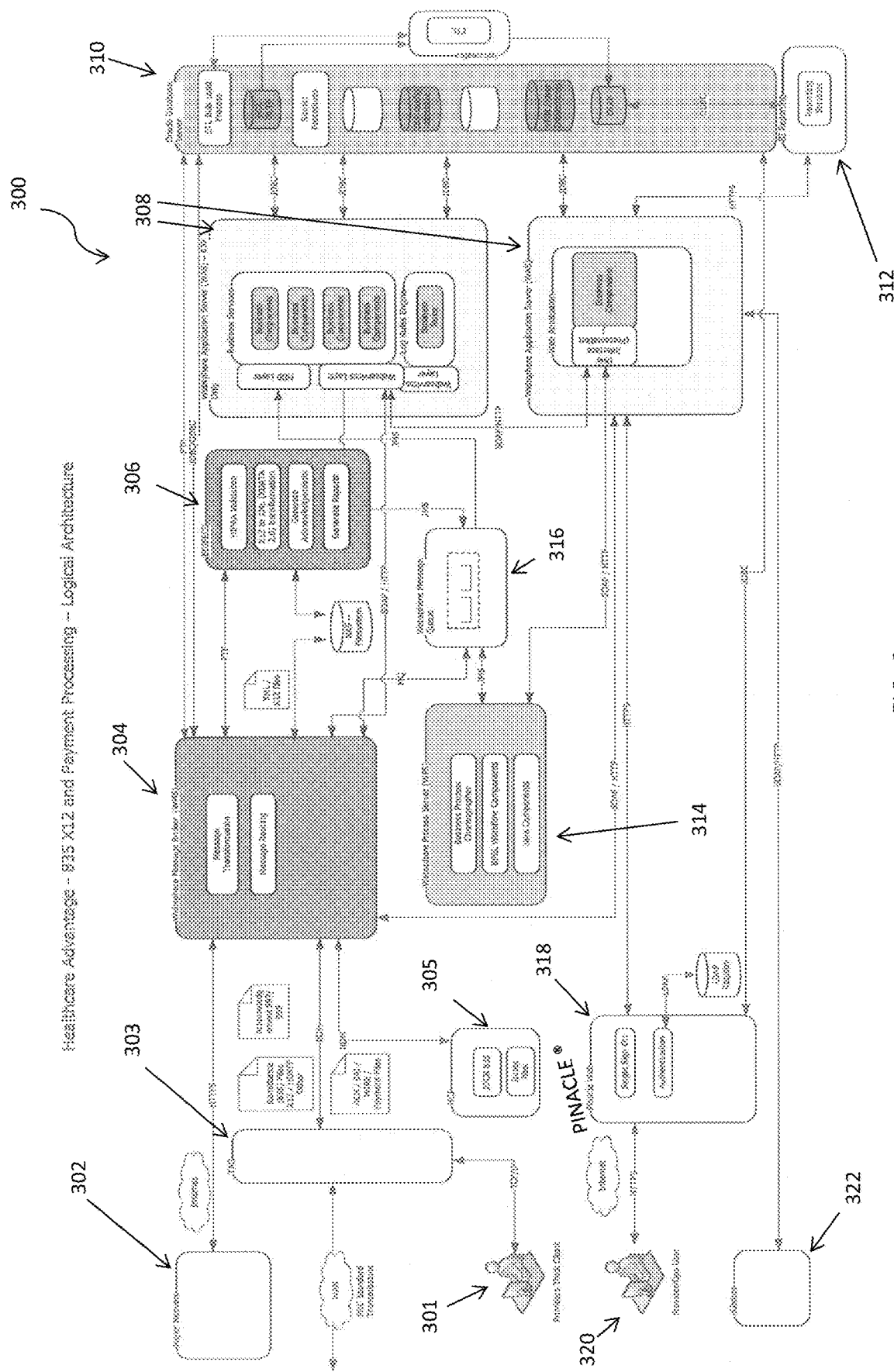
FIG. 3 illustrates a logic architecture of an exemplary network configuration for use with the system and method, in accordance with a preferred embodiment of the present disclosure.

Referring now to FIGS. 1-3, a network architecture, a system, and a logical architecture diagram of an exemplary system for reconciling a healthcare payment account, in accordance with a preferred embodiment of the present disclosure, are disclosed.

The network architecture of FIG. 1 illustrates a system, which includes a host system 12 in communication with one or more client devices $C_1, C_2, \ldots, C_i$ 14 (hereinafter referred to as "clients 14") via a communications network 16. The communications network 16 may be the Internet, although it will be appreciated that any public or private communication network, using wired or wireless channels, suitable for enabling the electronic exchange of information between the client(s) 14 and the host system 12 may be utilized.

According to exemplary embodiments, the host system 12 may be implemented by an institution, (hereinafter referred to as a 'host institution') such as for example, a financial institution, and can be configured to provide network-based product and service features to users (e.g., customers of the host institution that access the host system 12) associated with the client(s) 14. The customers can be individual customers, users responsible for managing financial accounts of a healthcare provider, or an entity associated with managing one or more financial accounts of a healthcare provider.

In preferred embodiments, the client(s) 14 may include any form of mobile or portable network-enabled computing device configured to transmit and receive information via the communications network 16 using wired or wireless connections. Client(s) 14 is/are capable of receiving user input via an input device. According to embodiments, the input device may be one or more of a touch-sensitive display such as a touch screen interface, a keyboard, a microphone, or a pointing device such as a mouse or stylus (see input devices 229 of FIG. 2). A client 14 may also include a display device (see display devices 228 of FIG. 2 and display 1630 of FIG. 16) capable of rendering an interactive Graphical User Interface ("GUI"), such as any of the GUIs discussed herein. The input device allows a user to interact with exemplary GUIs described below (e.g., FIGS. 7A-8A and 13-15) to instruct the network 10 and systems 200 and 1600 (e.g., FIGS. 1, 2, and 17) to display and edit account information, which is then rendered in the display device. Alternatively, the GUIs may be rendered on a display device of one or more servers, such as the email server 34, transaction server 42, web server 18, application server 20, and database server 22, as shown in FIG. 1.

The terms 'console display', display, 'display screen', and screen may be used interchangeably herein to refer broadly and inclusively to any type of display device or screen coupled to or integrated with a computing device for displaying content viewable by a user of the computing device, such as a user of a client 14. The client 14 may be a mobile computing client 14A or 14B. Such a display screen may include a touch-screen liquid crystal display (LCD) for example. The GUI of a mobile client 14A or 14B may be viewed on a display. In other embodiments, the GUI may viewed on a display of a server (e.g., a server console) such as consoles of servers 18, 20, 22, 34, or 42 shown in FIG. 1, a desktop computer (e.g., a PC monitor), or a laptop display, such as display devices 228 of clients 14 and 14A.

With any of the GUIs described and illustrated herein, the user interface and consoles may be rendered in a dedicated, native interface. In alternative embodiments, the console interface may be web based and rendered within a web browser. In other embodiments, a console interface can be displayed on server or workstation displays having a touch-sensitive (e.g., touch screen) display. For ease of explanation, the operation of the GUIs, displays, and console interfaces may be discussed in the context of a computing device platform with an input device such as a mouse or pointing device (including a touch-screen), but is not intended to be limited thereto. Examples of such computing device platforms include, but are not limited to, OSX server and workstation operating systems (OSs) from Apple, Inc.; WINDOWS® server and workstation OSs from the MICROSOFT™ Corporation; UNIX-based OSs, and Linux OSs, such as, but not limited to, Linux from RedHat™ Inc.

In alternative embodiments, the disclosed GUIs may be rendered on a display 228 of a mobile client 14 implemented as a mobile computing device such as, but not limited to, a personal digital assistant (PDA), an iPhone™, an iPod™ touch, or iPad™ tablet device, a device operating the Android operating system (OS) from Google Inc., a device running a MICROSOFT™WINDOWS® Mobile or Phone OS, a device running a Symbian OS, a device running a PALM OS®, a BLACKBERRY® device running a Blackberry OS from Research In Motion ("RIM"), a smart phone, a hand held computer, a netbook computer, a palmtop computer, a laptop computer, an ultra-mobile PC, or another similar type of mobile device capable of processing instructions and receiving and transmitting data to and from users and other computing devices.

One skilled in the art will appreciate, with the benefit of the present disclosure, that the GUIs illustrated in the exemplary embodiments may be readily adapted to execute on a display of mobile device platforms and operating systems, a computer terminal, a display of a client 14, a display console of a server, or other display of a computing device. Thus, the exemplary GUIs may be rendered on a display of mobile clients 14A and 14B using an online application, within a web browser session, on a display console of a server, or on a display of a client 14 running an online banking application.

In exemplary embodiments, a client 14 may be, but is not limited to, a personal computer (PC), a Personal Digital Assistant (PDA), a tablet computing device, an iPhone™, an iPod™, an iPad™, a device operating the Android operating system (OS) from Google Inc., a device running the Microsoft Windows® Mobile OS, a device running the Microsoft Windows® Phone OS, a device running the Symbian OS, a device running the webOS from Hewlett Packard, Inc., a mobile phone, a BlackBerry® device, a smartphone, a hand held computer, a netbook computer, a palmtop computer, a laptop computer, an ultra-mobile PC, a portable gaming system, or another similar type of mobile computing device having a capability to communicate via the communications network 16. Certain embodiments of clients 14 are depicted in FIG. 2, which is described below.

The host system 12 may be based on a multi-tiered network architecture, which may include one or more of a web server 18 (Tier 1), an application server 20 (Tier 2), and a database server 22 (Tier 3). According to this embodiment, the web server 18 corresponds to the first tier of the host system 12, and is configured to communicate with the communication network 16 via a border firewall 24 and with the application server 20 via an application firewall 26. The web server 18 can be configured to accept information requests, such as, for example, HTTP requests, from one or more of the client(s) 14 via the communication network 16 and to provide responses thereto. The responses may include, for example, HTTP responses including static and/or dynamic HTML documents for providing a user interface ("UI") 28 to users via the client(s) 14. Additionally, the web server 18 may further be configured to authenticate each user before allowing access to the UI 28 and other resources associated with the host system 12. Authentication may be performed, for example, by validating a received account identifier ("ID") or user name and a corresponding password. The ID/user name and password may be input in the UI 28 using an input device of the client 14.

The application server 20 corresponds to the second tier of the host system 12, and may be configured to communicate with the web server 18 via the application firewall 26 and with the database server 22 via an internal firewall 30. The application server 20 may host one or more applications executing logic to provide account reconciliation service features to each user via their respective user interfaces (UIs) 28. The application server 30 may receive account credentials (e.g., an account ID/user name and password), input and selections (e.g., a request to access particular account features) from the UI 28 of each client 14 via the web server 18. Based on this and other information received from the client(s) 14, applications hosted by the application server 30 may be invoked to perform financial transactions (e.g., transfer funds between accounts, retrieve account balances, schedule payments for bills/payables, link accounts, create new accounts, etc.) and generate corresponding informational content (e.g., transfer confirmations, account balance information, bill payment confirmation, account creation confirmation, etc.). Information regarding such transactions may be communicated to the web server 18 and subsequently presented to the users using, for example, a dynamic web page or interactive GUI of the UI 28. Additionally, the application server 20 may also host an application for enabling users to conduct email communication with the host system 12 and other parties, as well as an application for enabling transactions and communications with payers.

In the embodiment shown in FIG. 1, the database server 22 corresponds to the third tier of the host system 12, and is configured to communicate with the application server 20 via the internal firewall 30. The database server 22 manages one or more databases $DB_1, DB_2, \ldots, DB_i$ 32 (hereinafter referred to as "databases 32"), which stores data to support one or more applications hosted by the application server 20 or elsewhere. Such databases may include, for example, account information databases, account configuration databases, new account opening databases, document identification/authentication databases, user information databases, user identification/authentication databases, user preferences/settings databases, as well as databases for storing other settings and/or configuration data. Database information requested by a particular application is retrieved from the databases 32 by the database server 22, communicated to the requesting application, and updated by the database server 22 as needed.

The host system 12 may further include an email server 34, which is configured to communicate with the application server 20. In some embodiments, the host name of the email server 34 is determined by a registered domain name of the host institution (e.g., xyzbank.com), but other nomenclatures may be used. The email server 34 may include an email client application configured to enable exchange of electronic communications between the client(s) 14 and one or more parties $P_1, P_2, \ldots, P_k$ 36 (hereinafter referred to as "parties 36") external to the host system 12 via a communications network 38. The communication networks 16, 38 may be a common communication network (e.g., the Internet).

Although only a single email server 34, transaction server 42, web server 18, application server 20, and database server 22 are depicted in FIG. 1, it is to be understood that the functionalities of one or more of these servers may be implemented cluster of computing devices operating in a cluster or server farm. One such example is described below with reference to the exemplary embodiment shown in FIG. 2, wherein multiple transaction servers 42 are used.

The parties 36 may be any person or entity with whom a user desires to communicate regarding particular aspects of a healthcare account or related financial matters generally. The user may have, or desire to have, a financial relationship with the parties 36. Such parties 36 may include, but are not limited to, paying parties 36 for accounts receivable. For example, parties 36 may include, but are not limited to, an existing or new customer of a healthcare provider, a merchant account (e.g., a credit card account the organization or business establishes for receiving credit card payments), a business partner, a government agency (in the case of tax refunds or incentives), an insurance company/agent (a "payer" in the case of payable claims), or other paying parties 36 having a financial relationship with the user's organization or business from which the organization receives incoming payments or transfers to a financial account associated with the healthcare provider or related business.

As illustrated in FIG. 1, the host system 12 may include an email firewall 40 disposed between the email server 34 and the communication network 38 to protect network traffic and electronic communications between the parties 36 and the host system 12. To supplement network traffic protection provided by the email firewall 40, the email server 34 may implement one or more policies and anti-virus scanning software for intercepting email (e.g., "spam" email) unrelated to financial matters and possibly including malicious content. A user may be allowed to view intercepted email and authorize trusted senders, such as a party 36.

The host system 12 may further include a transaction server 42 which is configured to communicate with the application server 20. The transaction server 42 typically includes a client transaction application for enabling transactions. For example, transactions may take place between the client(s) 14 (customers of the host institution) and one or more payers $V_1, V_2, \ldots, V_k$ 44 (hereinafter referred to as "payers 44") external to the host system 12 via a communications network 46. The communication networks 16, 38, 46 may be a common communication network (e.g., the Internet). The transaction 42 server includes functionality enabling customers to receive payment from any of the payers 44 directly to one of their financial accounts. When a transaction is authorized (e.g., by signature, by PIN number, etc.), the payer 44 may communicate an acknowledgement of payment to the transaction server 42 via the communications network 46. When an acknowledgement of payment is received from a payer 44, the transaction server 42 and/or the application server 20 may initiate appropriate steps to account for the payment from the payer 44 to a financial account (e.g., checking account, savings account, money market account, etc.) of the customer. According to certain embodiments, the payers 44 may include, for example, insurers/insurance agents and other payers 44 having an existing financial relationship with the user's entity from which the entity receives incoming payments to a financial account associated with the entity.

As shown in FIG. 1, a transaction firewall 48 is disposed between the transaction server 42 and the communications network 46 for protecting network traffic and communications between the payers 44 sent via the communication network 46 and the host system 12.

The client(s) 14 may be PCs and/or other network-enabled devices (e.g., cell phones, mobile phones, mobile tablets, PDAs, etc.) configured to transmit and receive information via the communication network 16 using a wired or wireless connection. The client(s) 14 may include a suitable browser software application (e.g., Internet Explorer, Internet Explorer Mobile, Chrome, Safari, Firefox, Blazer, etc.) for enabling the user to display and interact with information exchanged via the communication network 16. The client(s) 14 may, therefore, access and navigate static and/or dynamic HTML documents of the UI 28.

FIG. 2 depicts an exemplary system 200 in which cash account reconciliation associated with a healthcare provider may be performed. FIG. 2 is described with continued reference to the embodiment illustrated in FIG. 1. However, FIG. 2 is not limited to that example embodiment.

As shown in FIG. 2, the cash flow management system 200 can be configured to view, edit, and create cash flow timelines between and among a plurality of clients 14, including mobile client devices 14 and a plurality of transaction servers 42 through communications sent via communications networks 16, 38, and/or 46. The transaction server 42B can be any type of server or computing device capable of serving data from database 32B to one or more client devices 14, including the mobile clients 14A and 14B depicted in FIG. 2. For example, the transaction server 42 can include, but is not limited to, a computer or a cluster of computers that may be a part of a server farm.

As depicted in FIG. 2, the display devices 228 of the client(s) 14 can differ depending on the type of computing device used as a particular client 14. For example, a display device of a tablet device, netbook, or laptop such as client 14A is typically an integrated LCD screen, which is often smaller than a monitor or console such as the display device 228 for a workstation or desktop PC such as client 14. Similarly, the display device 228 of a mobile computing device, such as client 14B may be a relatively small display such as mobile phone display.

The input devices 229 may also vary depending on the characteristics of a particular client 14 and its display device 228. For example, the input device 229 of a tablet, netbook, or laptop client 14A may include a relatively small physical or touchscreen keyboard, an integrated camera, track pad, and/or microphone, while the input device 229 of a desktop PC or workstation client such as client 14 will typically include a physical QWERTY or Dvorak keyboard and a mouse. Also, for example, an input device 229B of a mobile client 14B will typically lack a full physical keyboard, and may instead comprise one or more of a touch-screen keyboard, a microphone, an integrated camera, a track pad, a scroll wheel, a track ball, a T9 keyboard, a button, and a touch screen display device. Any of the display devices 228 may be a touch screen display. It is to be understood that in the case of a touch screen interface, the input device 229 may be anything capable of interacting with the touch screen, including a user's fingers, which may be used to select, slide, drag, and resize (e.g., expand, maximize, shrink, and/or minimize) interactive UI elements through pointing, pinching, and scrolling gestures.

The UI 28 may be tailored to or customized for a particular client 14 based on the capabilities of the platform used by that client 14. The platform comprises physical capabilities of the client's 14 computing device, such as memory capacity in terms of random access memory (RAM) and read only memory (ROM), central processing unit (CPU) capabilities in terms of clock speed and available processing capacity, available storage in terms of disk space or flash memory, communications capabilities in terms of current wired and/or wireless network connectivity, and a communications interface (see, e.g., communications interface 1624 of FIG. 16), such as a network interface card (NIC) of the computing device, capabilities of the display device 228, and capabilities of the input device 229. These physical capabilities and others can be determined based on a manufacturer, model number, serial number, a Media Access Control address (MAC address) and/or another unique identifier of a computing device used as a client 14.

The platform of a client 14 also comprises software and firmware components, such as an operating system (OS) running on the client 14, Internet browser(s), native software applications installed, and privileges/permissions associated with the client 14. The privileges/permissions may be controlled by the host system 12 based on a user and/or an entity associated with the client 14, and can include data access, communications, and application execution privileges.

According to exemplary embodiments, the UIs 28A and 28B for mobile clients 14A and 14B may be rendered as streamlined 'mobile friendly' versions of the 'full' UI 28 for ease of use on relatively small display devices 228. Mobile friendly UIs 28A, 28B may have reduced capabilities and/or display a lesser level of detail, as compared to UI 28. A mobile friendly UI 28B may also be tailored to accept input from input devices 229B for a specific platform of a mobile client 14B. The mobile friendly UIs 28A and 28B may be automatically selected by the system 200 in response to detecting one or more platform characteristics of a particular mobile client 14A or 14B. Alternatively, a user of a mobile client 14A or 14B may be prompted within the full UI 28 to opt-in to using the mobile friendly UIs 28A and 28B in response to detecting that the client 14A or 14B is accessing the host system 12 via a mobile computing device. In cases where a user's mobile client 14A, 14B has display devices 228 and input devices 229A, 229B capable of using the UI 28, the user may not wish to use the mobile friendly UI 28A or 28B.

Figure 7A:
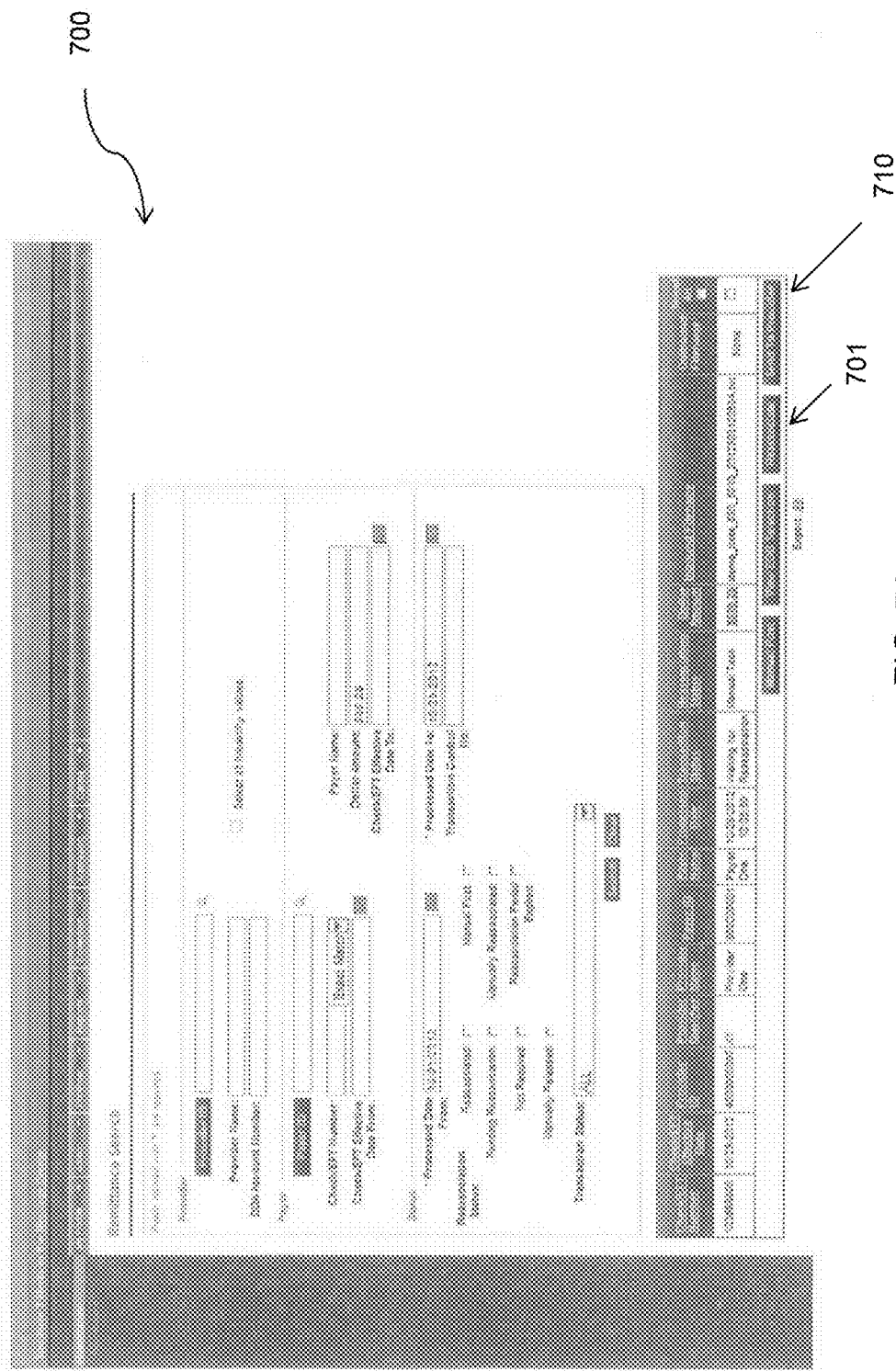
FIG. 7A illustrates an exemplary GUI enabling a user to search the database and effect a manual match of an explanation of benefits file and a payment, in accordance with a preferred embodiment of the present disclosure.
Figure 8A:
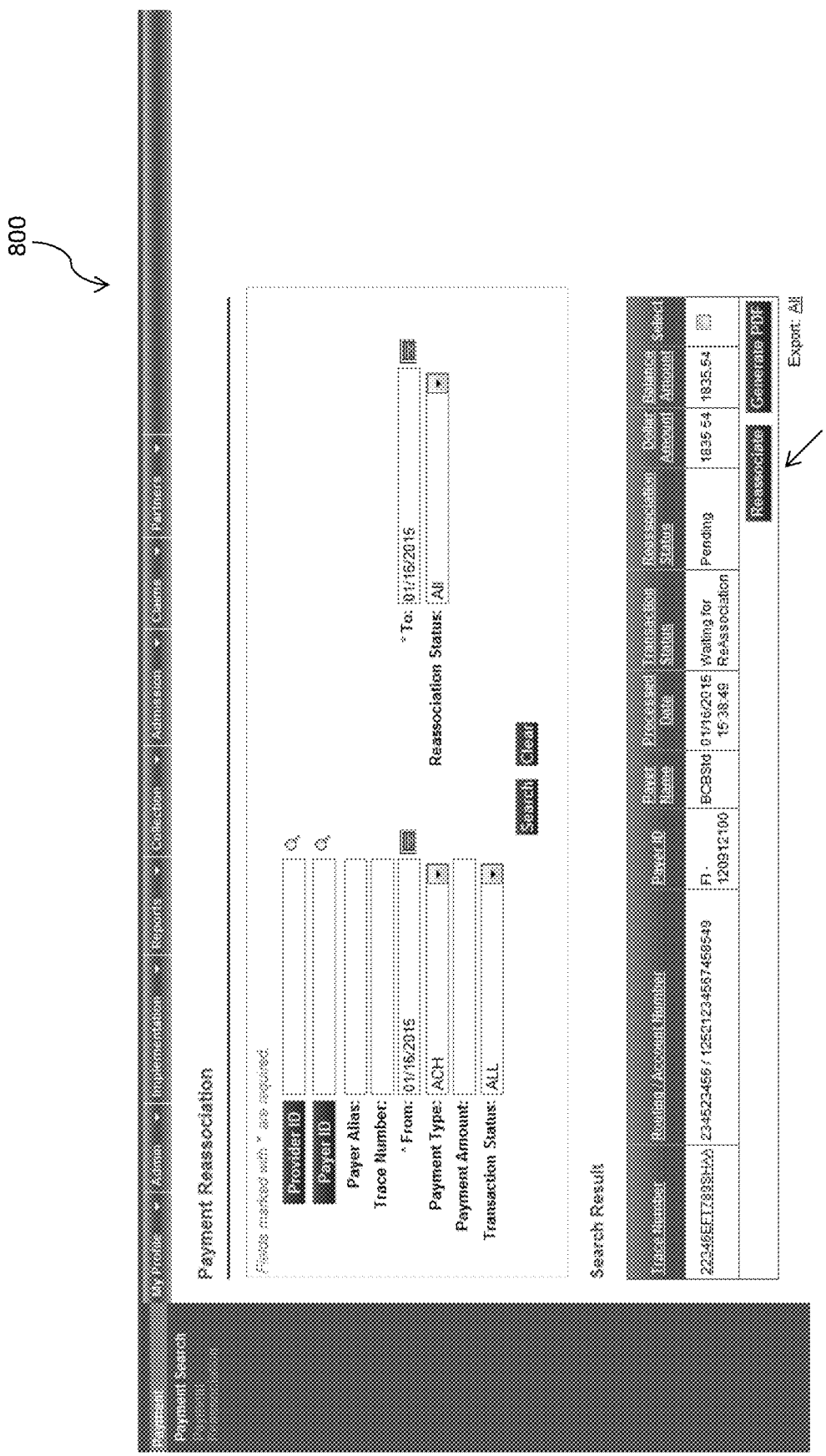
FIG. 8A illustrates an exemplary GUI enabling a user to search the database and effect a manual match of a payment and an explanation of benefits file, in accordance with a preferred embodiment of the present disclosure.

According to exemplary embodiments, such as those depicted in FIGS. 7A and 8A for example, the UI 28 allows operations and transactions to be performed and displayed with a greater level of detail than the mobile friendly UIs 28A and 28B. For example, the granularity of transactions or simulated transactions may be finer (i.e., more detailed) in the UI 28 as compared to the mobile friendly UIs 28A and 28B.

The one or more of the communications networks 16, 38 and 46 may be any network or combination of networks that carry data communications. Such networks may include, but are not limited to, wireless data networks such as a Wi-Fi, 3G, and a 4G/LTE network. In addition, the communications networks 16, 38 and 46 shown in FIGS. 1 and 2 may include, but are not limited to, a wired Ethernet network, a local area network (LAN), a medium area network, and/or a wide area network (WAN), such as the Internet. In exemplary implementations of system 200 including wireless networks, one or more of the communications networks 16, 38 and 46 may support protocols and technology including, but not limited to, Internet or World Wide Web protocols and/or services. Intermediate network routers, gateways, or servers (not shown) may be provided between components of the architecture 10 and the system 200 depending upon a particular application or environment.

With continued reference to the exemplary embodiment of FIG. 2, multiple transaction servers 42 may be used as part of the system 200. For example, a first transaction server 42B may be employed to process Cash In transactions or for processing replicas of Cash In transactions. In alternative embodiments, the functionality and components of transaction server 42B may reside on a single transaction server 42, such as, for example, the transaction server 42 shown in FIG. 1.

With continued reference to FIG. 2, the transaction server 42B may be used to process a healthcare provider entity's Cash In transactions or replicas of Cash In transactions, such as, but not limited to, credits, accounts receivable, merchant account payments from the entity's customers, and incoming transfers, including those from external accounts not handled by the host system 12. Data for these Cash In transactions (or replicas thereof) may be stored in and retrieved from a Cash In database 32B. Although the Cash In database 32B is depicted in FIG. 2 as being hosted locally on the transaction server 42B, it is to be understood that the Cash In database 32B may be hosted on a server remote from the transaction server 42B, such as a remote RDBMS.

The transaction server 42B may communicate with other components of the system 200 via communications networks 16, 38 using a communications interface device 211. For example, communications between the transaction server 42B and clients 14, the application server 20, and the email server 34 may be handled by the communications interface device 211. In the embodiment illustrated in FIG. 2, the transaction server 42B includes a transaction processor 221 that may comprise modules of computer-executable instructions or program logic that use information from and store data in the Cash In database 32B. The modules may also obtain from and send information to other components of the system 200 using the communications interface device 211 to communicate via communications networks 16, 38. As shown in FIG. 2, because this data may include sensitive financial account information, communications may be received from clients 14 via a border firewall 24 between the communications network 16 and the host system 12, and/or an email firewall 40 disposed between the email server 34 and the communication network 38.

FIG. 3 illustrates the logic architecture 300 of an exemplary network configuration for use with the system and method for reconciling a healthcare payment account. Initially, a payer network 302 is connected to a Websphere Message Broker ("WMB") 304. The payer network 302 may be connected to the WMB 304 based on any appropriate communication network, for example, the Internet. The WMB 304 receives, analyzes, and validates incoming files, such as files that contain EOB information, for example a Direct 835 file 900, and then determines where they are to be routed based on the analysis. As shown in FIG. 3, the incoming files may be received via the payer network 302 of a healthcare payer (e.g., an insurance provider). The WMB 304 operates to ensure that a complete file is received and is valid for further transmission. The WMB 304 can be used for healthcare related transaction, or other forms of data transactions.

In addition, files containing EOB or other information may also be received from a healthcare provider. The Providers Thick Client 301 represents a location from which healthcare provider information may be received. The Providers Thick Client 301 may be connected directly or indirectly to the WMB 304 based on any appropriate communication network, for example, the Internet. According to the example of FIG. 3, the Providers Thick Client 301 is connected through a Transmission Automation Group ("TAG") 303 infrastructure, which provides in-bound and out-bound file management of data transmissions. EOB information may be received for example, in the form of data files transmitted directly by payers (electronic remittances or Direct 835s 900) or physical documents that undergo an optical character recognition ("OCR") process. For example, an IOCR 835, or a Direct 835 file 900, may be images that are taken from a data location, such as a client lockbox, and formatted according to electronic template documents, which may be stored in a HCI module 305. Payment files, such as ACH, BAI, and Wire payment files may be provided by the Providers Thick Client 301.

The WMB 304 is connected to a Health Insurance Portability and Accountability Act ("HIPPA") validation tool, which is labeled as EDIFECS 306. EDIFECS 306 is a validation tool confirming that the files sent to the WMB 304 contain the correct syntax, and that the files are properly balanced. In a preferred embodiment, there may be seven layers of HIPPA validation. Preferably, the EDIFECS 306 accomplishes syntax validation by checking the punctuation of an incoming file.

The EDIFECS 306 may be configured to transform incoming files into a format that is easier to process by a host system 12. For example, The EDIFECS 306 may transform an incoming file from X12 format to XML format. XML is extensible markup language and is understood to be a more generally supported computer language. Preferably, the EDIFECS 306 is capable of generating acknowledgments and reports based on the information received.

The EDIFECS 306 passes files to the Websphere Application Server(s) ("WAS") 308. The WAS 308 stores various business components and business rules. Preferably, a user interface described in the present application is an application layer that is run by the WAS 308. The WAS 308 may then provide information to a reporting module or it may transfer information to a database server, such as the Oracle database server 310, which provides access to various databases. The Oracle database server 310 may provide the information on a pre-determined or as needed basis. For example, information may be provided to the Oracle database server 310, hourly, daily, weekly, or more or less frequently as needs arise. The Oracle database server 310 provides access to the information in the various databases to generate reports based on adjustments made by a healthcare payer, as well as to provide data for other operations.

Also as shown in FIG. 3, the Websphere Process Server ("WPS") 314 is a component that monitors internal business processes and manages the flow of data files from one application to another within the infrastructure. The Websphere Message Queue 316 is a component that controls message flow between the WMB 304, EDIFECS 306, WAS 308, and the WPS 314. In addition, a Business Intelligence ("BI") reporting component 312 allows for reports to be generated based on data stored in the databases accessed by the Oracle database server 310. Preferably, an image warehouse labeled as eGistics 322 is be provided, which enable access to images of original EOB information by a user.

Also shown in FIG. 3, the PINACLE® Web 318 is an exemplary information reporting system for a user 320 (labeled as "Provider/Ops user") of the system 300. In preferred embodiments, PINACLE® Web 318 enables more than just healthcare transactions, which may include, but are not limited to, financial transactions, such as wire transfers and balance checks. The user 320 may be able to access the PINACLE® Web 318 through any appropriate communication network, such as, for example, the Internet. PINACLE® Web 318 provides access and authorization for the user 320 to access the WAS 308 and associated user interface discussed herein.

System and Method

Figure 4:
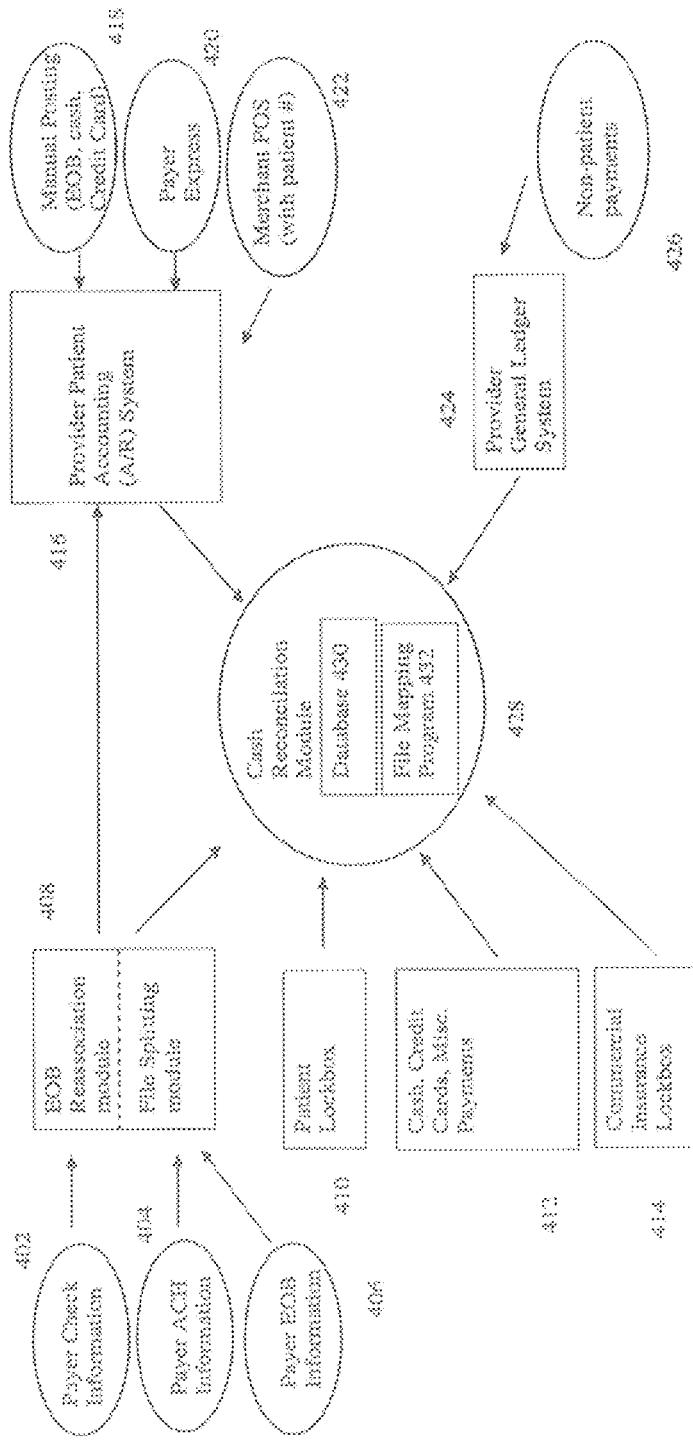
FIG. 4 illustrates a component diagram, in accordance with a preferred embodiment of the present disclosure.
Figure 5:
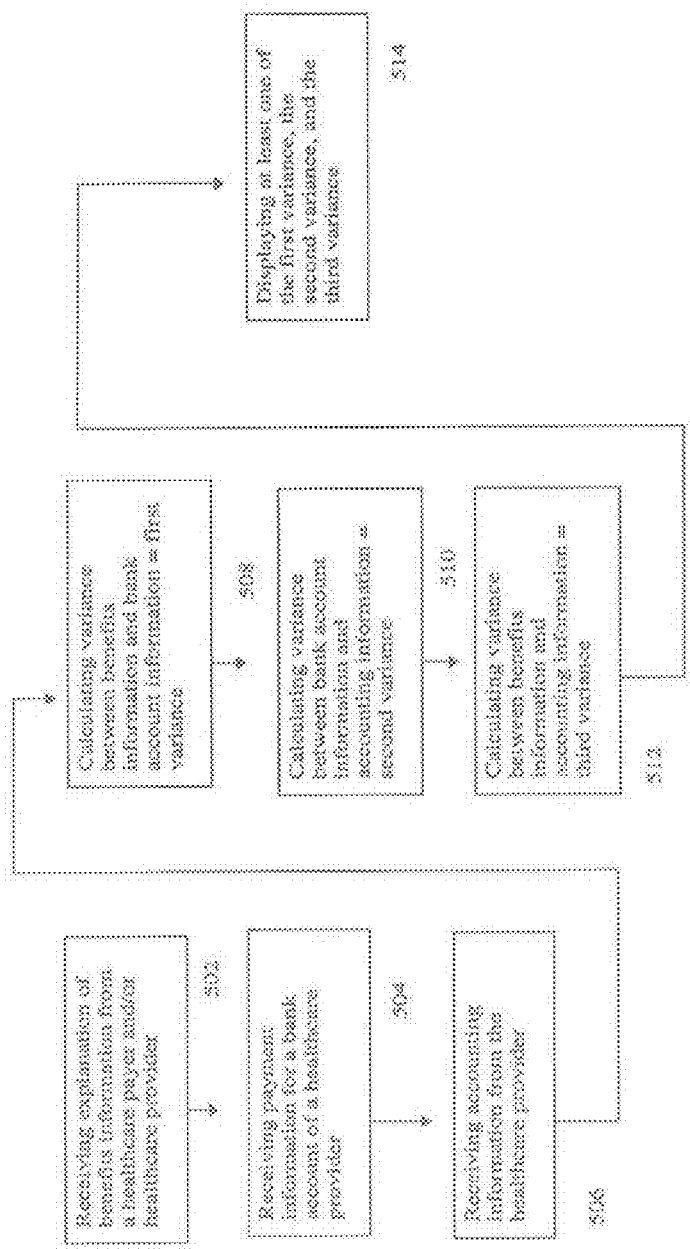
FIG. 5 illustrates a flowchart depicting steps by which reconciliation of a healthcare account may occur, in accordance with embodiments of the present disclosure.

As shown in FIG. 5, and by reference to FIG. 4, a system and method for reconciling a healthcare payment account are described. A Cash Account Reconciliation module 428 receives a first electronic file that comprises EOB information from a healthcare payer and/or healthcare provider at step 502. A second electronic file that comprises payment information for a bank account of a healthcare provider is received at step 504. A third electronic file that comprises accounting information from the healthcare provider is received at step 506.

The Cash Account Reconciliation module 428 calculates a first variance that comprises a variance between the first electronic file and the second electronic file at step 508, calculates a second variance that comprises a variance between the second electronic file and the third electronic file at step 510, and calculates a third variance that comprises a variance between the first electronic file and the third electronic file at 512. The Cash Account Reconciliation module 428 may be programmed to display at least one of the first variance, the second variance, and the third variance at step 514. The Cash Account Reconciliation module 428 may be programmed to generate and display a report of at least one of the first variance, the second variance, and the third variance to a user as well.

As illustrated in FIG. 4, the receipt of the first, second, and third electronic files may be based on automated import of data from various bank systems 402, 404, 410, 412, 414, healthcare clearinghouse systems 406 and healthcare provider systems 416, 424 into a Cash Account Reconciliation database 430 located within the Cash Reconciliation Module 428. A healthcare clearinghouse system 406 (e.g., Relay-Health and Emdeon) may perform other functions, such as process claims and other healthcare files. A provider patient A/R system 416 may receive information regarding manual posting of payments 418, such as from cash and/or credit cards, a patient payment Internet portal ("payer express" system) 420, and from a Merchant Point of Service ("POS") 422 location. The data imports from the bank systems 402, 404, 410, 412, 414, healthcare clearinghouse systems 406 and healthcare provider systems 416, 424 may occur at the end of a business day or at another pre-determined time schedule. Additionally, the data from various bank systems 402, 404, 410, 412, 414 and healthcare provider systems 416, 424 may include EOB payment extract data from a Direct 835 file 900, Lockbox BAI check files, similar lockbox files, BAI files containing ACH/EFT and deposit ticket information, payment posting data from client A/R systems, and/or payment posting data from a client's general ledger system 424, which includes payments received that are not related to a medical claim of a patient. The general ledger system payments 424 may be for example, non-patient payments 426 received from a health club or cafeteria associated with the healthcare provider.

In summary, the multi-system Cash Account Reconciliation database 430 automates data import from various bank and client systems. Data imports include EOB payment extract data, Lockbox BAI check files or similar lockbox files, BAI or other format files containing ACH/EFT and deposit ticket information, payment posting data from client A/R systems, payment posting data from a client's G/L systems.

In a preferred embodiment, the payer EOB information 406 is received and matched with payment information by the Reassociation and/or File Splitting module(s) 408 before calculation of the variances is performed. The payment information may comprise payer check 402 or electronic payment information (e.g., ACH or EFT) 404, which represents payment for services that had been received at a financial account (e.g., bank account) of the healthcare provider. In a preferred embodiment, the system may be programmed to enable character-recognition and communicate encoded information derived from the character-recognition via a host adapter. In a preferred embodiment, the host adapter is a host channel adapter (HCA) configured to communicate encoded information via magnetic ink character recognition (MICR). A MICR reader device identifies and records the encoded information (e.g., MICR lines of a check). A HCA connects the host system 12 to other networks via InfiniBand interface cards. The system may also be programmed to automatically process MICR lines for implementation of check reassociation. As illustrated in FIG.

4, the Reassociation and File Splitting modules 408 may be combined as a single module or be separate modules.

The reassociation and/or file splitting processes are what enable the disclosed system and method to integrate standard bank data with healthcare specific transaction date so as to facilitate cash reconciliation in a system-agnostic and cost effective manner. Implementation of these processes via the disclosed system and method enables separating and balancing data from different accounting entities/accounts receivable ("A/R") systems, which is preferably performed via a three-way matching process. One skilled in the art will appreciate, with the benefit of the present disclosure, that a two-way matching process, four-way matching process, etc. may be used without deviating from the teachings of the disclosed system and method. The three-way matching process, which is described in detail below, improves matching rates while reducing computational and process steps that would otherwise be required while performing reconciliation.

Referring now to FIGS. 6A-D, flowcharts and flow diagrams of reassociation, in accordance with a preferred embodiment of the present disclosure, are disclosed. In a preferred embodiment, the Reassociation module 408 performs the function of matching files (commingled data and/or non-commingled data) with payment information in the form of, for example, check or ACH/EFT payments posted to a healthcare provider's bank or financial account(s). The matching process may include matching of multiple payment types, including, but not limited to, lockbox checks and ACH types PPD, CCD, and CCD+, and other EFTs. The matching criteria may be dynamic and/or pre-defined to increase an automated match rate.

Figure 6A:
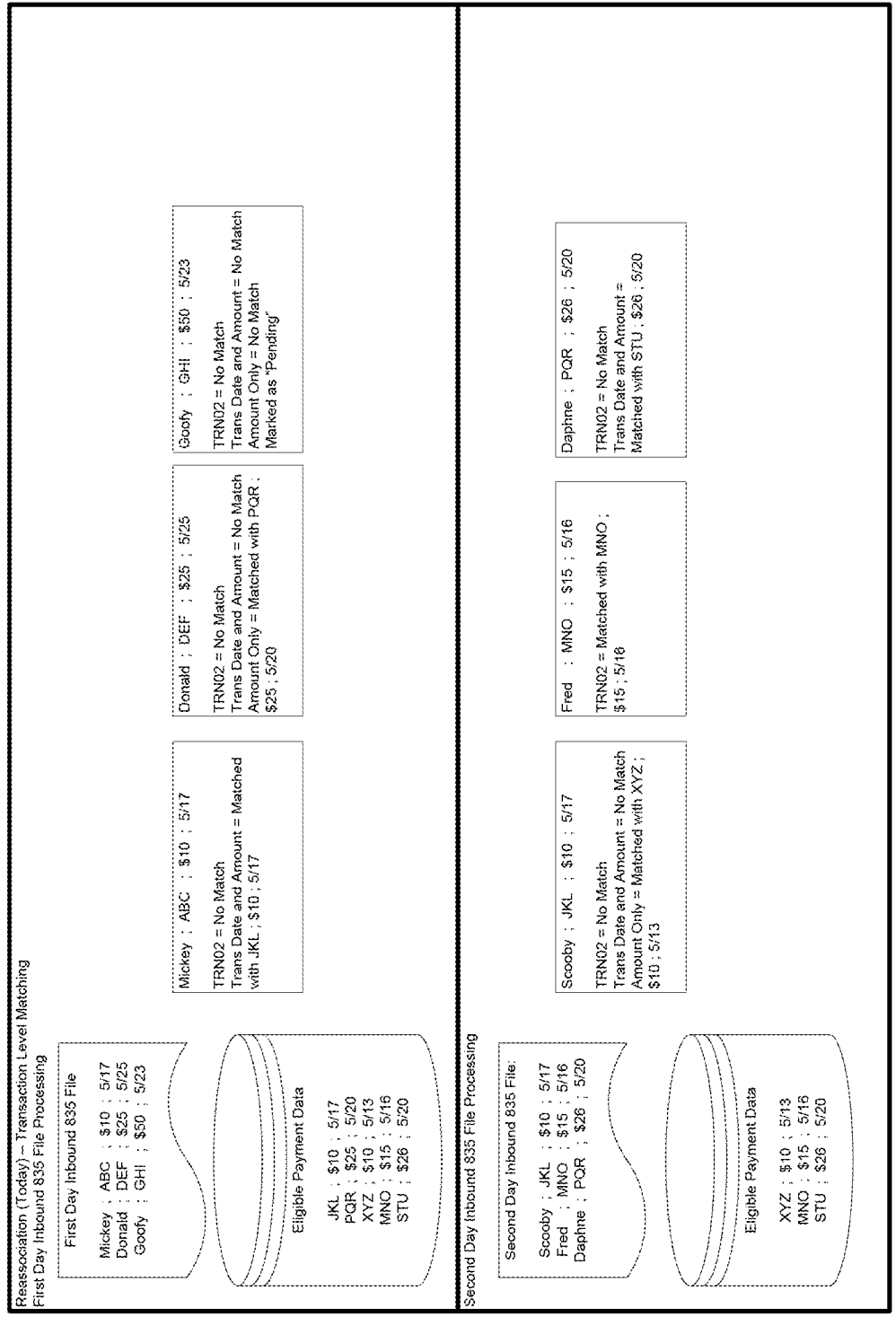
FIGS. 6A and 6B illustrate flow diagrams depicting transaction and file level matching through reassociation, in accordance with a preferred embodiment of the present disclosure.

As shown in FIG. 6A, a reassociation process may occur in the following manner. A Provider/Payer match is performed by gathering information separately from the Direct 835 file 900 and from the payment to ascertain a match/mismatch based upon an ID qualifier (both the for Provider and Payer) in the Direct 835 file 900. For example, with an ACH transaction, the Payer ID within the transaction itself provides the Payer information, and the DDA enables the system to determine a facility (i.e., a Provider). With a check transaction, the account number and routing number combination enables the system to determine the Payer, whereas the lockbox information enables the system to determine a facility (i.e., a Provider). Once the Provider/Payer match is determined, matching is determined by the Trace Number (TRN02) and Amount. If no match is found, then matching is determined by Transaction Date and Amount. If there is still no match found, then matching is determined by Amount only. This matching may be done by going through the file and considering each transaction separately. If no match is made, the transaction is marked as "Pending" to be set aside while the next transaction in the file is considered. Note that this reassociation process is performed by using the Trace Number only, as opposed to the entire TRN segment. In other words, this matching is not done by considering the file as a whole. Consequently, a match may be made by Amount only. Considering the file as a whole is preferred because it generates more accurate matches by matching at the Trace Number level, which is described below.

Figure 6B:
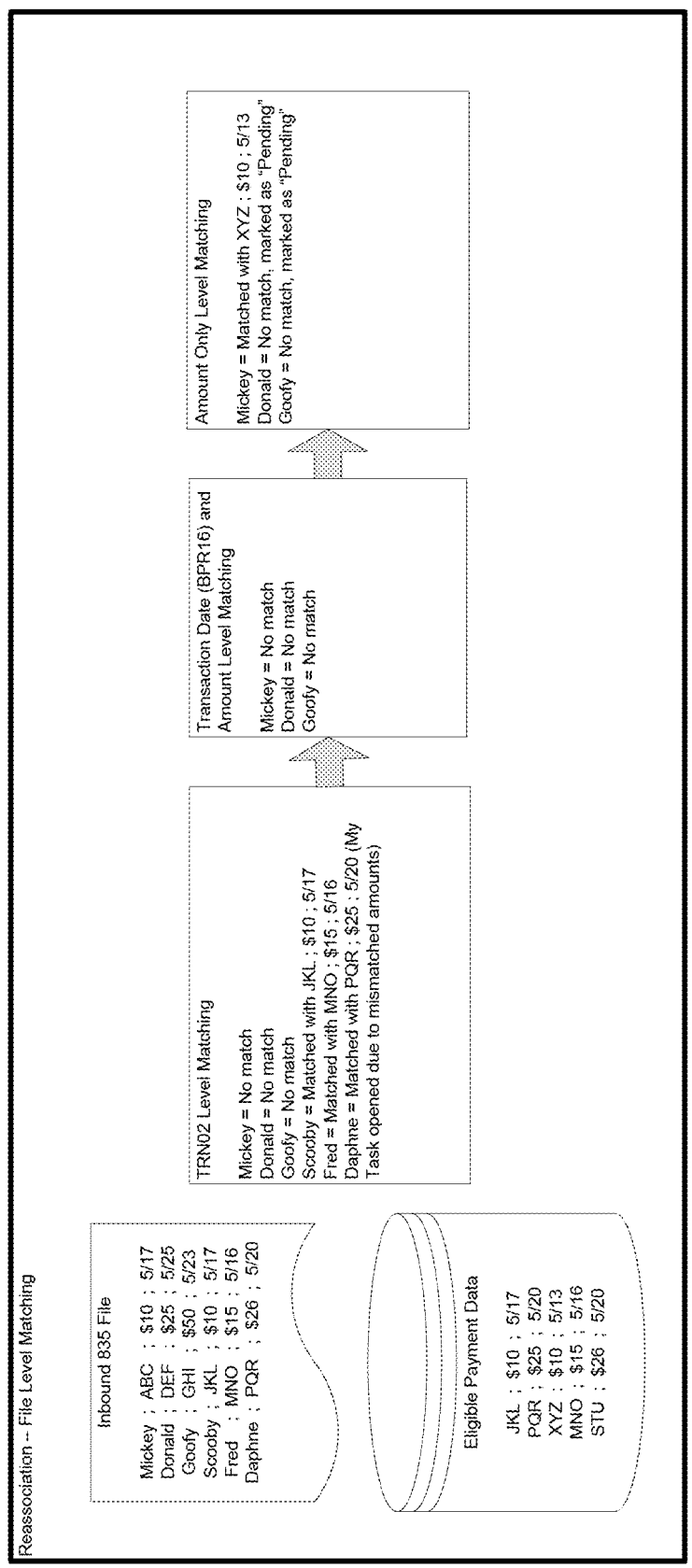

Referring now to FIG. 6B, reassociation while considering the file as a whole, is disclosed. While considering the file as a whole, each level of matching is applied to an entire file (transaction by transaction) before moving to the next transaction rather than applying all levels of matching to a single transaction before moving onto the next transaction. In addition, other matching levels may be included. In an exemplary process, matches are first made by the entire TRN segment (as opposed to just the Trace Number) that exists in the Direct 835 file 900 and in the Electronic Fund Transfer (EFT) addenda. The other matching levels are made by Trace number, followed by Transaction Date and Amount, and then by Amount only. The system may then seek a remittance-payment match for more than one facility linked to the same DDA account number.

Figure 6C:
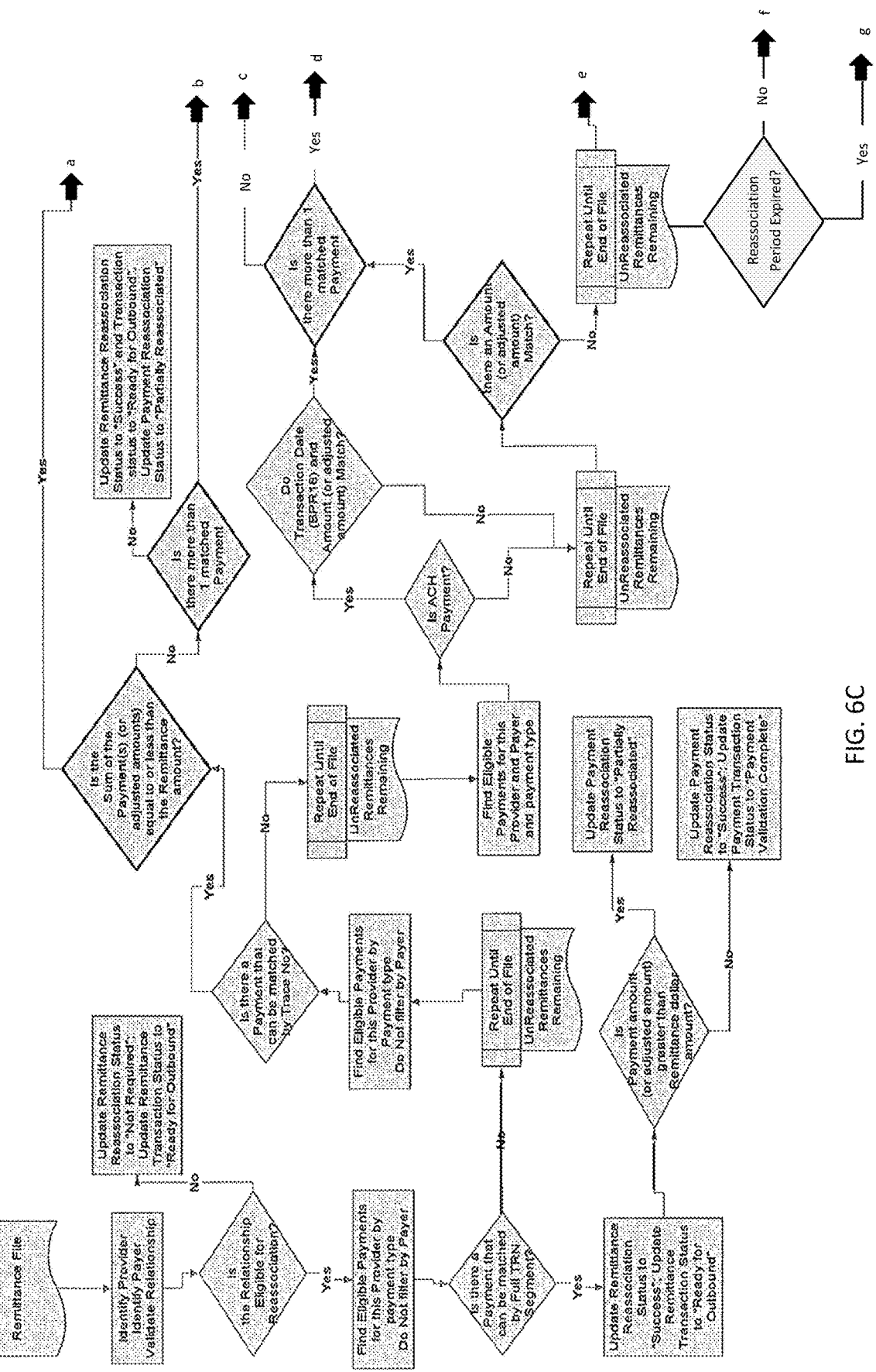
FIG. 6C illustrates a flowchart depicting steps by which data in an explanation of benefits file is evaluated using rules based logic so that the transactions in the file may be accurately matched with one or more check or electronic payment, in accordance with a preferred embodiment of the present disclosure.
Figure 6C:
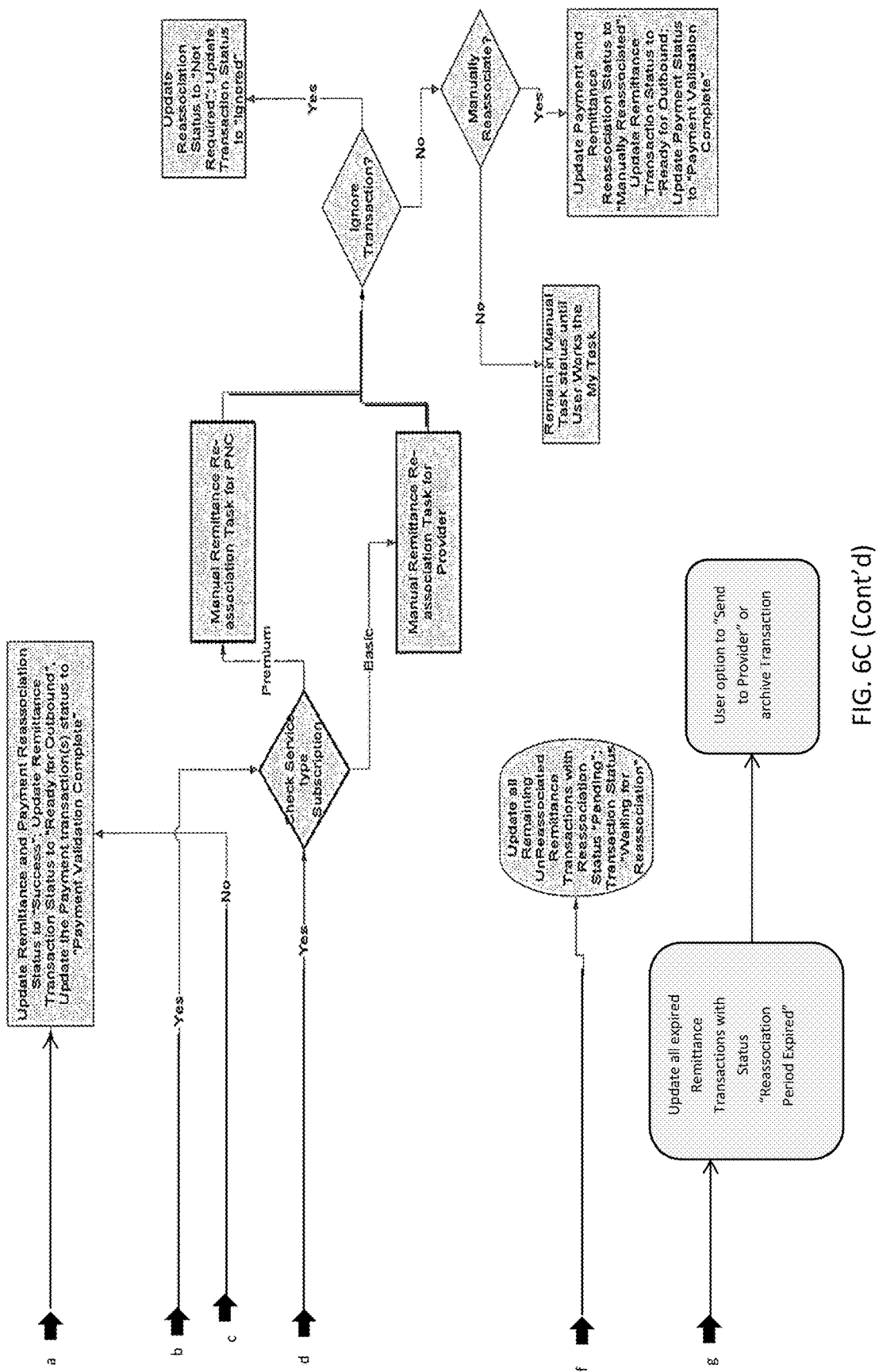

FIG. 6C shows an exemplary remittance reassociation process conducted by the matching process depicted in FIG. 6B. As a remittance file enters the system, a Provider/Payer identification/validation occurs. Eligible reassociation relationships and ascertaining eligible payments by payment type are performed. This is followed by a determination of whether a payment can be matched by an entire TRN segment.

In a first possible path wherein a match can be made, the remittance status is updated to "success." That successful match is used to determine if the payment amount is greater than the remittance amount, and if so then the remittance status is updated to "partially reassociated". If there is no difference, then the remittance status is updated to "success".

In a second possible path wherein a match could not be made, the process repeats, but the payment match is performed with the Trace Number this time. A successful match is used to determine if the sum of the payments amount is equal to or less than the remittance amount, and if so then the remittance status is updated to "success". If the sum of the payments amount is greater, then a determination is made as to whether there is more than one matched payment. If there is not, then the remittance status is updated to "partially reassociated". If there is more than one payment, then the system enables manual remittance reassociation. In the second possible path, if the payment cannot be matched by Trace Number, then the system determines if the payment is an ACH. If the payment is an ACH, then payment match is performed with Transaction Date and Amount. If a match is found, the system determines if there is more than one matched payment. If there is not, then the remittance status is updated to "success". If there is more than one payment, then the system either enables manual remittance reassociation or performs a match with the Amount. If the payment is not an ACH, the process is repeated until the end of the file.

In either path, the process is repeated until it reaches the end of the file, at which point a successful reassociation, partial reassociation, or unreassociated remittance is ascertained.

Figure 6D:
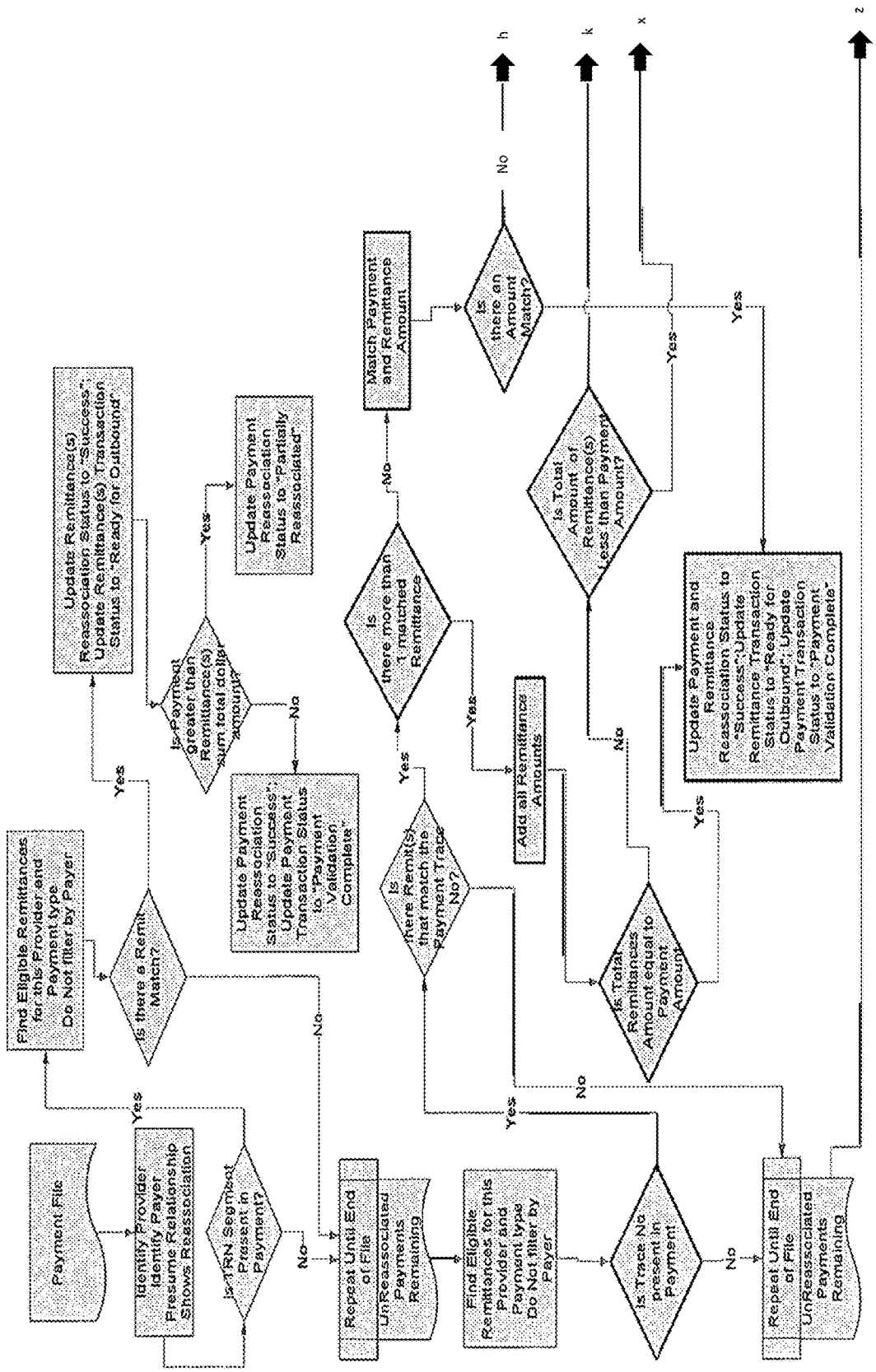
FIG. 6D illustrates a flowchart depicting steps by which information accompanying a payment is evaluated using rules based logic so that the payment may be accurately matched with one or more explanation of benefits files, in accordance with a preferred embodiment of the present disclosure.
Figure 6D:
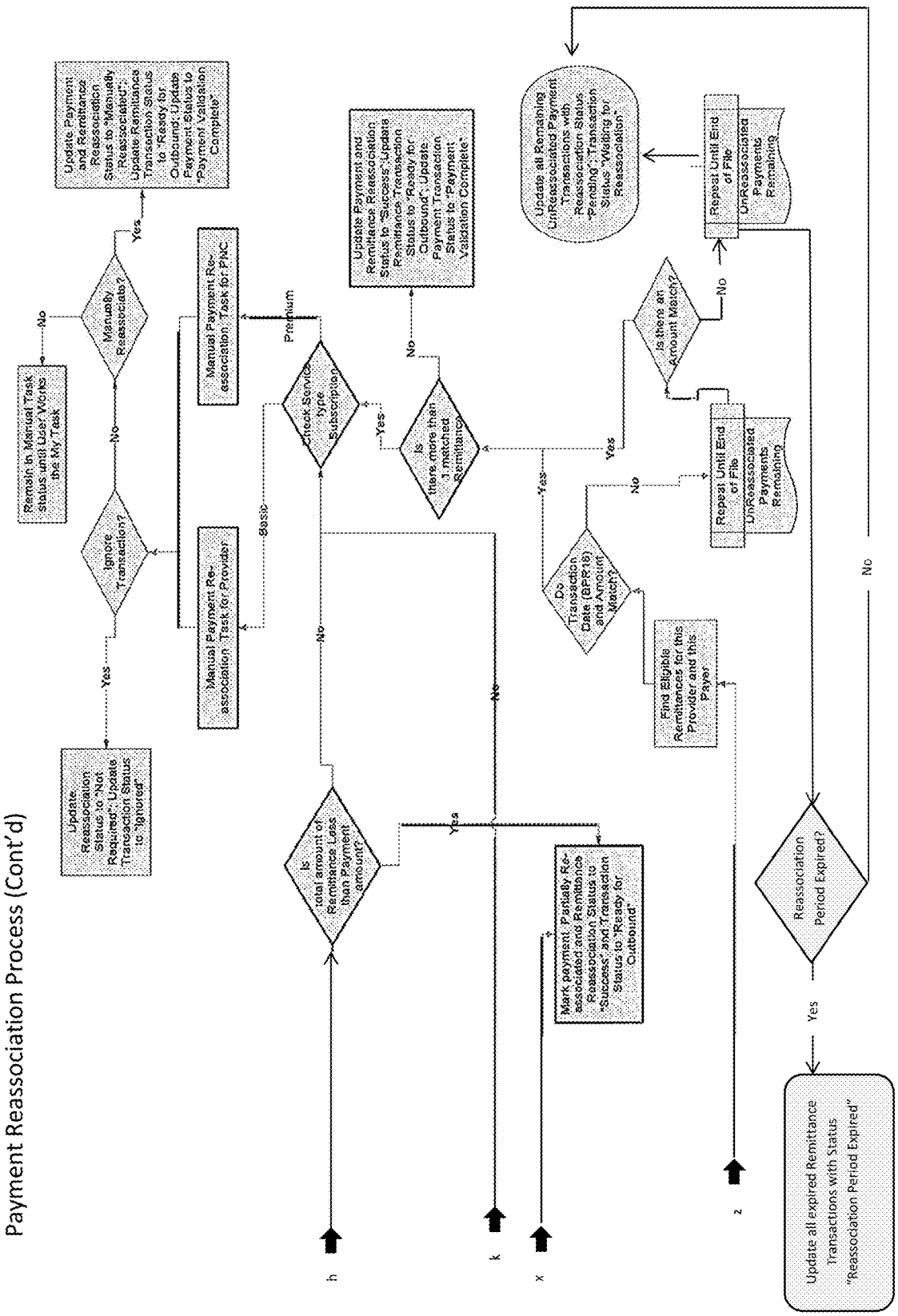

FIG. 6D shows an exemplary payment reassociation process as by the matching process depicted in FIG. 6B. As a payment file enters the system, a Provider/Payer relationship is determined. The system searches for a TRN segment within the payment. Although the determining steps are different, FIG. 6D discloses possible paths just as FIG. 6C does, which are used in the payment reassociation process. These include using the TRN segment, Trace Number, Transaction Date and Amount, and Amount as matching criteria. For example, in a first possible path wherein no TRN segment is present in the payment, the process is repeated until the end of the file. Then the system determines if there is a match by EFT Trace/Check Number only. Then the system determines if the Transaction Date and Amount match. If not, then the system determines if there is an Amount match. If not, then the transaction status is updated to "Waiting for Reassociation". Again, in either path, the process is repeated until it reaches the end of the file.

As is described below, the results of these matching paths are communicated via displays and reports generated by the system to enable a user to perform reconciliation activities.

Figure 7B:
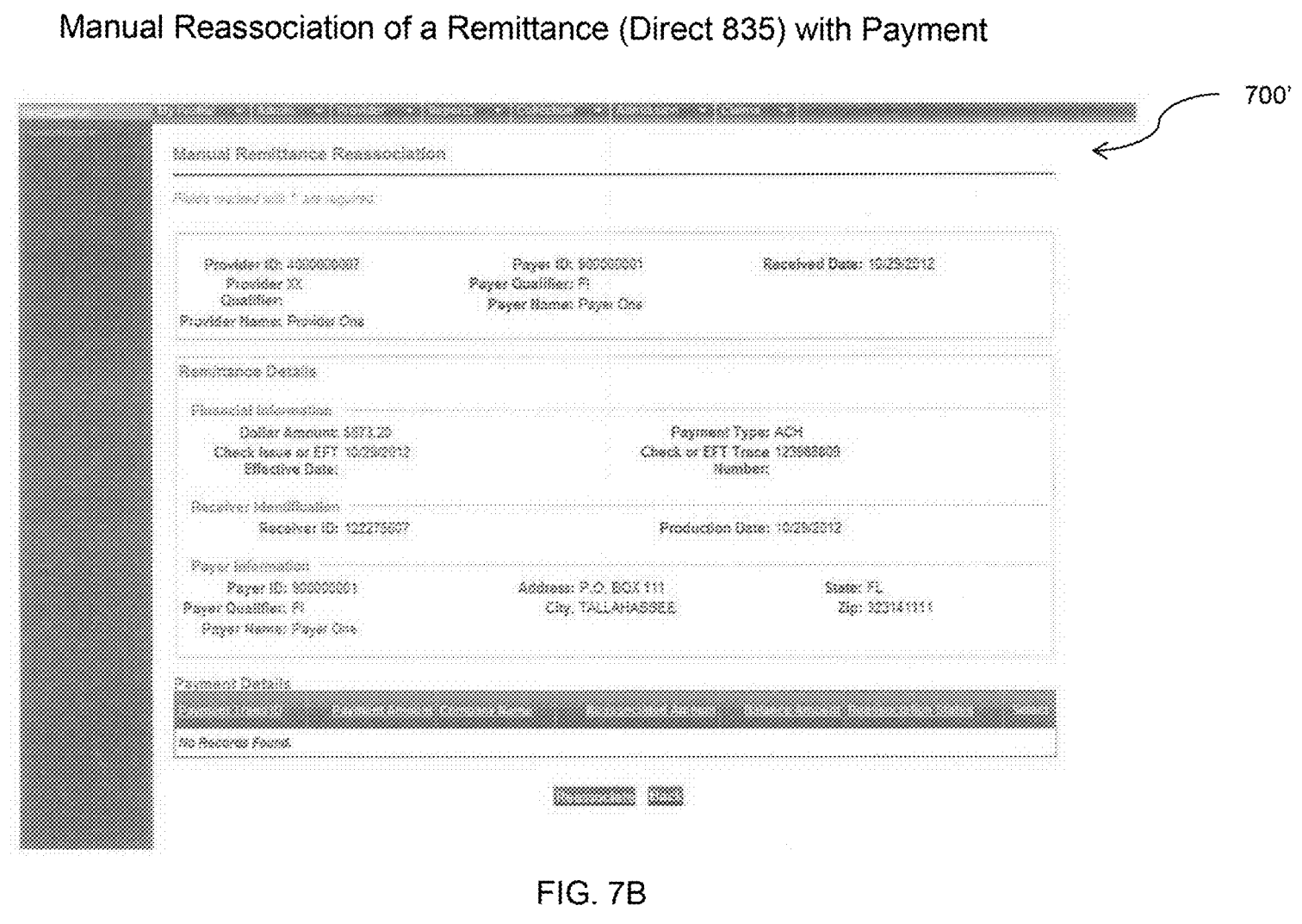

Matching may be effectuated regardless of whether a healthcare payer uses disparate pre-defined or specified match criteria or uses standardized criteria, such as HIPAA specifications for example. Further, if specifically desired payer data is available in the EOB files, matching can also occur by Tax ID or National Provider ID ("NPI") with associated reporting at the business office or facility level. Moreover, if an EOB file or payment is not matched automatically, the system provides graphical user interfaces (GUIs) to enable users to effectuate a manual match of an EOB file with a payment. FIG. 7A illustrates the GUI 700 enabling a user to search the database and effectuate a manual match of an EOB file and a payment. FIG. 7B illustrates a report 700' generated by the EOB data matching process effectuated by FIG. 7A and via the process depicted in FIG. 6C. A user reaches the report 700' by selecting a transaction and clicking the REASSOCIATE button 701 in GUI 700. A file may be transmitted to the Provider even if there is no match by actuating the Send to Provider 710 button, as shown in FIG. 7A. FIG. 8A illustrates a graphical user interface (GUI) 800 enabling a user to search the database and effectuate a manual match of a payment and an explanation of benefits file. An example of a report 800' generated following the matching the EOB information with the payment information is provided in FIG. 8B. A user reaches the report 800' by selecting a transaction and clicking the REASSOCIATE button 801 in GUI 800.

As indicated in the report 800', a reassociation status column 802 demonstrates a "Manual Task" in cell 804; however, the status column 802 may display "successful" to indicate a successful match between the EOB information and the payment information, or may display "Follow Up Task" to indicate to a user that further action is required, or other indicators such as "Reassociation Period Expired". As by way of example, an unmatched file may be indicated by "Reassociation Period Expired", where a user may then transmit the file via the Send to Provider 710 button or leave the unmatched file in the system. As by way of another example, if there is more than one potential match for a payment or remittance, a "Manual Task" may be displayed. In a preferred embodiment, the system may be programmed to transmit notifications associated with "Manual Tasks". These notifications may include electronic messaging, such as, but not limited to, email notifications. One skilled in the art will appreciate, with the benefit of the present disclosure, that the system may be configured to communicate with users and report to users about various other activities and statuses of those activities. This may be by, but is not limited to, alerts, texts, email, instant messages, textual displays, graphical displays, and/or other electronic, magnetic, optical, or electromagnetic messaging sent via communication networks 16, 38, 46 and communication paths 1626 (see FIG. 16). Communications may comprise notifications reflecting actions that should be taken by a user. A communication may be saved or exported to a digital messaging system. This may be, but is not limited to, email, instant messenger, and/or a Short Messaging System (SMS). A communication may be saved or exported to a Personal Information Manager (PIM) or a Personal Data Manager (PDM). This may be, but is not limited to, Microsoft Outlook. The system may be configured to enable a user to communicate to another user via a digital messaging system.

Communications may be transmitted between users and/or between a user and the system. Communications may be sent periodically, due to a condition met, in response to an action initiated by a user, in response to an action completed by a user, and/or based upon a user's status. Communications may be sent automatically. Communications may be sent discriminatorily.

Figure 8C:
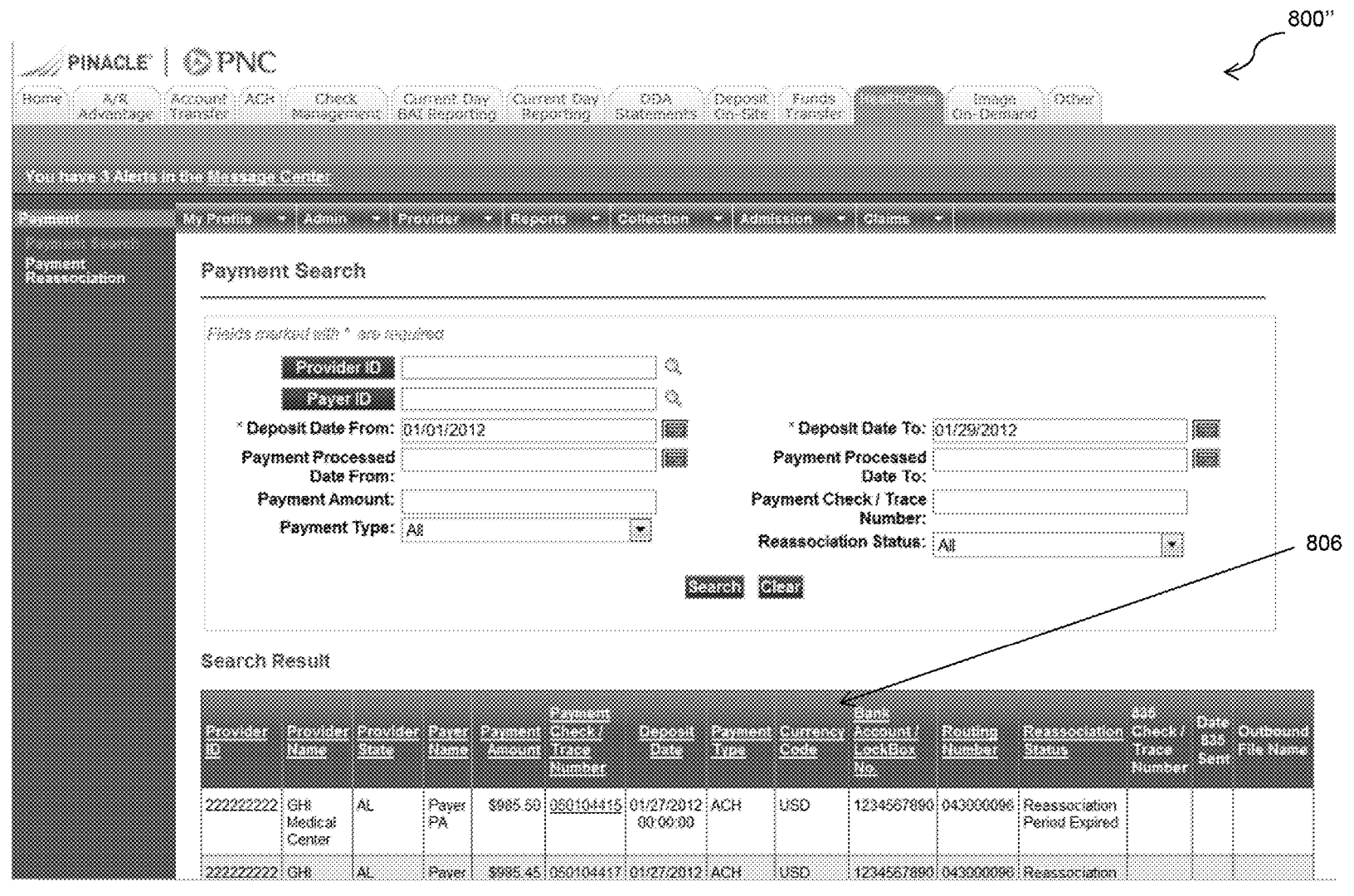

Referring now to FIG. 8C, a payment search report GUI 800" is disclosed, which enables a user to search all payments, regardless of reassociation status, create a custom report, and export it to Excel or an accounting system to facilitate reconciliation or accounting processes outside of the Cash Reconciliation Module 428. For example, a report may be exported to a general ledger system. GUI 700 serves this purpose for remittances. GUI 800" may be programmed with additional fields 806 (e.g., currency code) to facilitate a general ledger import.

In summary, the reassociation process performs automatic matching of EOB files (commingled data and/or non-commingled data) to check or ACH/EFT payments posted to provider bank accounts. The matching process includes matching of multiple payment types. Dynamic and/or pre-defined matching criteria may be used to increase an automated match rate. Matching may be effectuated regardless of whether payers use disparate pre-defined or specified match criteria or use standardized criteria. If payer data is available in the EOB files, matching can also occur by Tax ID or National Provider ID ("NPI") with associated reporting at the business office or facility level. The process includes various user interface options that allow users to manually reassociate unmatched EOB files and/or payments or to override the reassociation process and have unmatched EOB files transmitted.

Referring now to FIGS. 9-12, the File Splitting module 408 splits the original EOB file into separate files by accounting entity and/or A/R system by using pre-defined data elements within the EOB file to identify how files should be split after the reassociation with the payment information is completed. The file splitting process interrogates an EOB file according to data segments contained therein, which then generates sub-files in accordance with predefined business rules for each provider entity. This enables segmentation of the EOB information based upon an accounting entity or billing/accounting system of the healthcare provider or the payer, thereby introducing flexibility in receiving and transmitting data to the appropriate accounting entity or billing/patient accounting system of the healthcare provider. Furthermore, provider level balance and patient payment entries that are not identifiable to a particular accounting entity or billing/accounting system may still be sorted.

For example, an EOB data file may contain patient level data that is contained in the CLPs, wherein the patient level data information may be sorted according to pre-defined alpha-numeric identifiers within the CLPs. A pre-defined identifier may be a prefix of the CLP 01/patient account number, or an identifier could be a consistent data string in the middle of the CLP 01/patient account number. An illustrative example can be seen in two CLP 01 segments: 12888845039 and 348888111. Both of these could be sorted based on the sequence of four "8s" starting in the third position of the CLP 01.

The new sub-files are then rebalanced and their totals are balanced to the payment amount indicated in the original EOB file. The plurality of rebalanced separate files is considered a complete payment file. If a particular alpha-numeric identifier does not match a pre-defined category, the CLP with that identifier is placed into an exceptions sub-file. Furthermore, Provider Level Balance ("PLB") payment information, which does not relate to an individual patient account, may also be placed into the exceptions sub-file. Accordingly, PLB segments and patient payment entries (also called CLPs) not identifiable to a particular accounting entity or system may be sorted into an exception sub-file. The system may be programmed to generate a separate Provider Level Balance (PLB) Adjustment Report 1500 (see FIG. 15), which provides a detailed list of PLB transactions sorted into the exception sub-file. PLB transactions are preferably listed in a separate detailed report as a research tool because they are often a source of cash reconciliation variances.

Referring back to FIGS. 9-12, an example of the file splitting process and payment extract process is described in more detail. This example uses an industry format of Direct 835 file 900 for the electronic transmission of EOB information; however, other formats may be used as well. The payment amount from an original Direct 835 file 900, as received from the payer, is recorded in the BPR segment 904 of the Direct 835 file 900.

Figure 10:
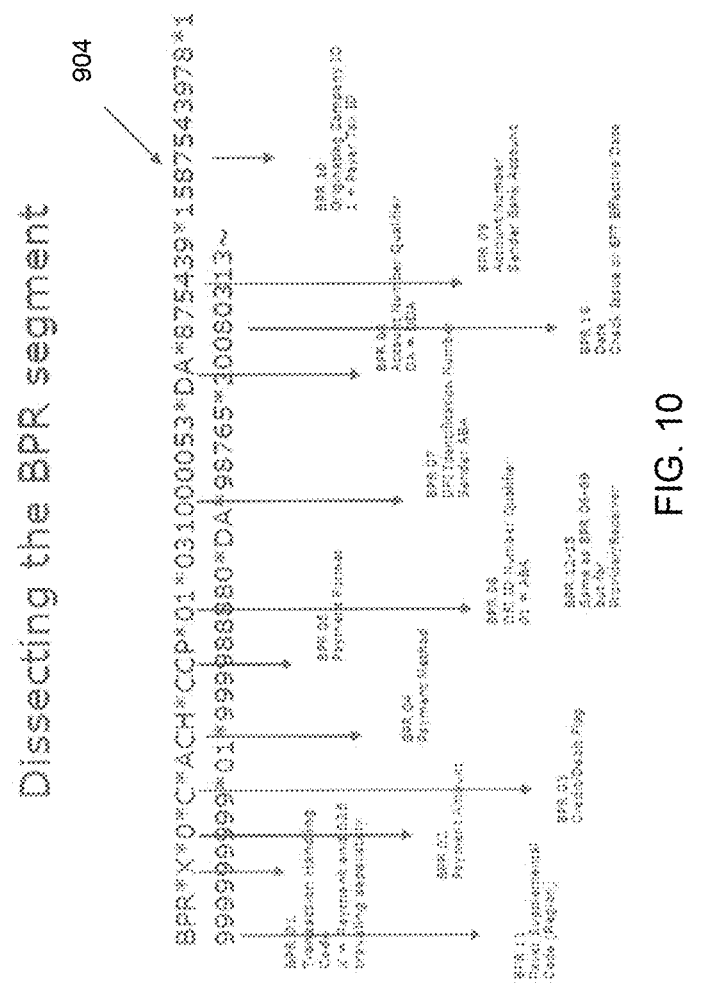

FIG. 10 illustrates the information carried in the BPR segment 904. The BPR segment 904 may include payment information from a payer, including, but not limited to, coding directed to payment method, an account number for a sender's bank account, and a check issue date or EFT effective date.

Figure 11:
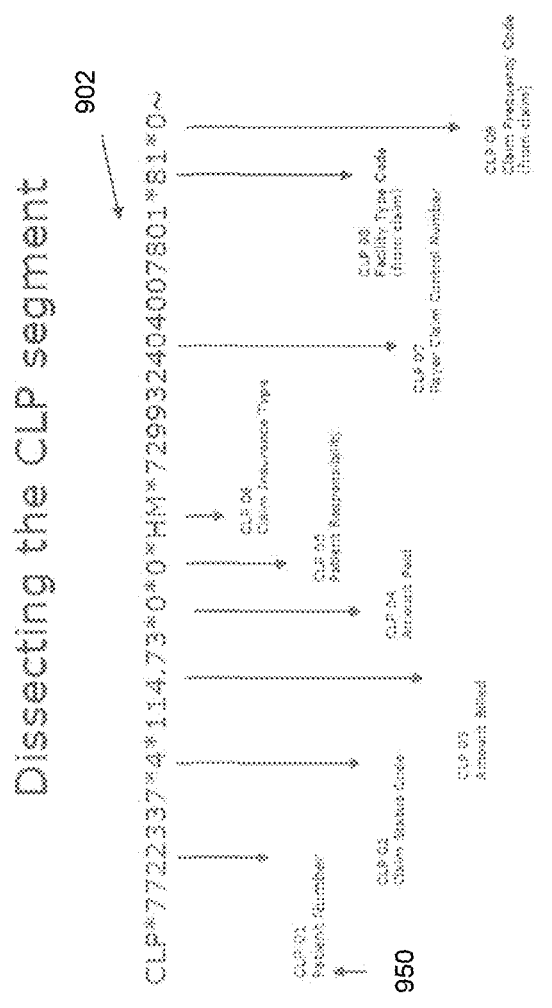

FIG. 11 illustrates the information carried in the CLP segment 902. In a Direct 835 file 900, each BPR segment 904 is followed in by a list of CLP segments 902 representing patient level information. As shown in FIG. 11, the CLP segment 902 may comprise an alpha-numeric pattern. The CLP segment 902 may include coding directed to patient information regarding payment of a medical claim, including, but not limited to, patient number, amount billed, and amount paid.

Figure 12:
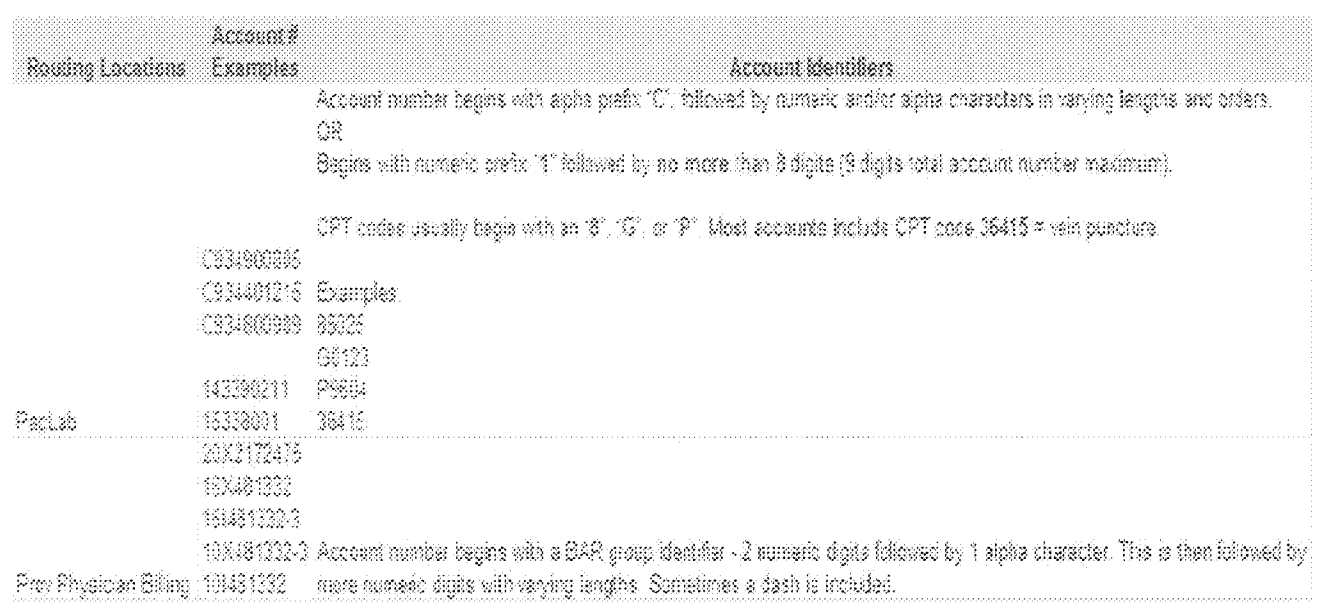

In the file splitting process, the CLP segments 902 from each original Direct 835 file 900 may be read and sorted by client accounting entity based on client-specific business rules. Illustrative examples of client account entity identification functions are demonstrated in FIG. 12. As shown in FIG. 12, a particular location may have a distinct account number (or patient account mask 1304—see FIG. 13) based on a first alphanumeric value or a group identifier of multiple alphanumeric patterns that are referenced when determining the location.

After sorting the records, a new Direct 835 sub-file for each group of accounting entity CLPs is created, and a new BPR segment is created for each new Direct 835 sub-file. The new BPR segment represents the total of all the patient payment information in the new file. Any CLP segments that do not meet the business rules established for that client plus any Provider Level Balance ("PLB") adjustments may be sorted into the exception sub-file. File Split Reports 1300 (see FIG. 13) and Provider Level Balance Adjustment Reports 1500 (see FIG. 15) may then be generated by the system for display to a user.

Figure 13:
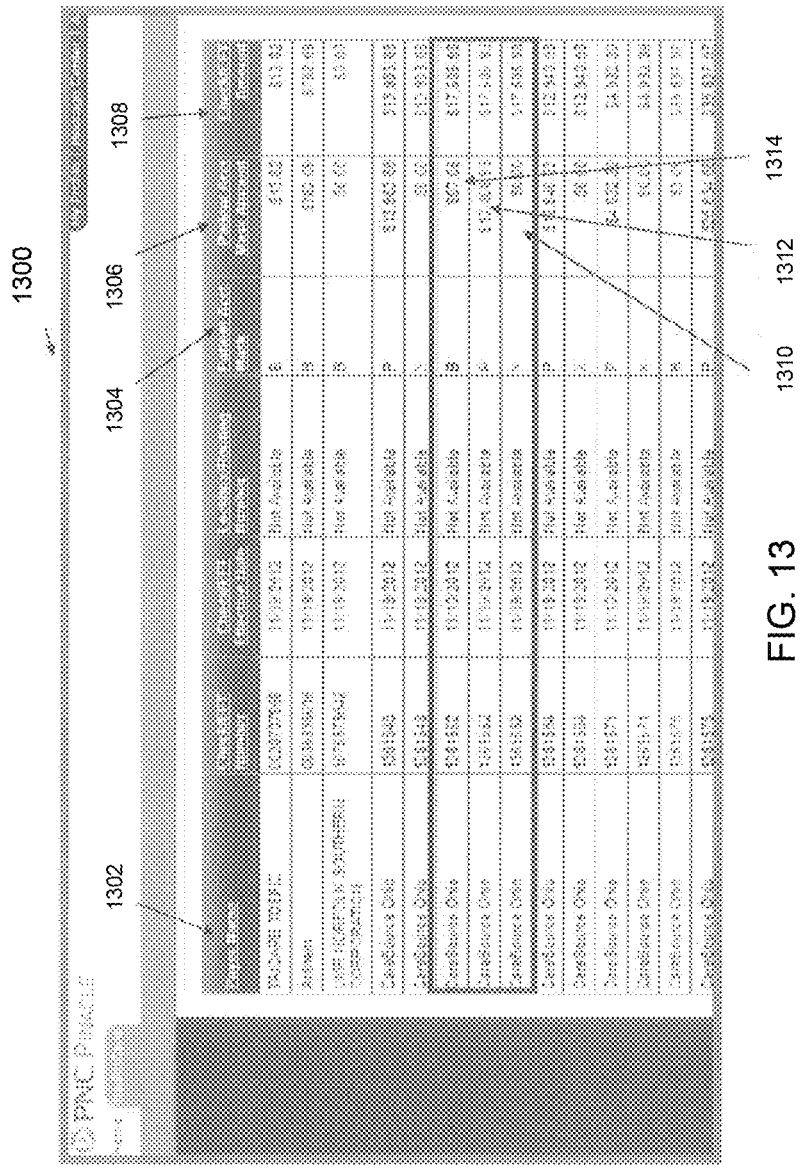
FIG. 13 illustrates an exemplary File Split Report that may be produced by the system and method, in accordance with a preferred embodiment of the present disclosure.

Referring now to FIG. 13, an illustrative example of a File Split Report 1300 is illustrated. The BPR segments for all newly created Direct 835 sub-files are totaled and rebalanced to the BPR total from the original Direct 835 file 900 received. Rebalancing the plurality of Direct 835 sub-files may be done based on at least one of an accounting entity and an accounts receivable system such that a total payment amount is calculated and the plurality of rebalanced separate files constitutes a complete payment file. The complete payment file is reflected on a File Split Report 1300, where the sub-files created for each original Direct 835 file 900 are listed.

The File Split Report 1300 contains information regarding details of the 835 sub-files created during the file splitting process, including but not limited to columns for the payer name 1302, the patient account mask 1304, the patient account mask amount 1306, and the Check/EFT amount 1308. In an exemplary File Split Report 1300 shown in FIG. 13, there are three rows 1310, 1312, 1314 that correspond to three 835 sub-files created during the file splitting process. Each of row 1310, 1312, 1314 has the same Check/EFT amount of "$17,505.98", indicating that the three sub-files files are related to an original Direct 835 file 900. A patient account mask 1314 of "B" indicates that, out of the total of $17,505.98, provider entity "B" has been paid $97.05. Patient account mask 1314 "P" indicates that, out of the total $17,505.98, provider "P" has been paid $17,408.93. A Patient account mask 1314 of "X" indicates that there is no PLB adjustment or exception record in the particular Direct 835 file 900 because row 1310 is zero.

In summary, the file splitting process splits the EOB file data into separate files by accounting entity and/or A/R system, while using pre-defined data elements within the EOB file to identify how the data should be split. New sub-files are created and retotaled, which are balanced to the payment amount indicated in the original EOB file. PLB segments and patient payment entries (CLPs) not identifiable to a particular accounting entity or system are sorted into an exception file. A host financial entity may work with healthcare providers to establish a program to identify entities or patient accounting systems via unique alpha numeric patterns in the CLP 01 data element 950 (i.e., a patient account number) of a Direct 835 file 900. An example of unique alpha numeric patterns in the CLP 01 data element 950 is illustrated in FIG. 11. Based on each provider's custom program, the splitting process may perform the following: 1) records the payment total amount from the BPR segment 904 from each Direct 835 file 900; 2) reads each CLP 01 segment 950 associated with the BPR segment 904, and associates the CLP 01 segment 950 with a healthcare provider entity or patient accounting system based on the alpha numeric patterns in the provider custom program; 3) sorts the CLP records, including all accompanying service lines that identify healthcare services and associated payments rendered for each patient encounter, by provider entity or patient accounting system into one or more sub-files, which may meet HIPAA standards for balancing and syntax; 4) sorts any CLP records not matching the custom provider program into an exception sub-file which meets HIPAA standards for balancing and syntax; 5) sorts any Provider Level Balance ("PLB") adjustment records for interest, recoupments of patient payments made in prior periods, or other reasons into the exception sub-file, which meets HIPAA standards for balancing and syntax; 6) recalculates new BPR segments for the sub-files so that each new BPR segment represents the portion of the original payment amount (from step 1 above) belonging to each provider entity, or patient accounting system, or the exception sub-file; 7) balances the total of the new BPR segments for the sub-files to the BPR segment from the original Direct 835 file 900 (in step 1 above) to ensure that the total patient payments sorted into the sub-files equals the total payment amount from the original Direct 835 file 900; and, 8) reports the original payment amount and the totals of all sub-files on the File Split Report 1300.

Exemplary User Interface for Healthcare Cash Account Reconciliation

Figure 14A:
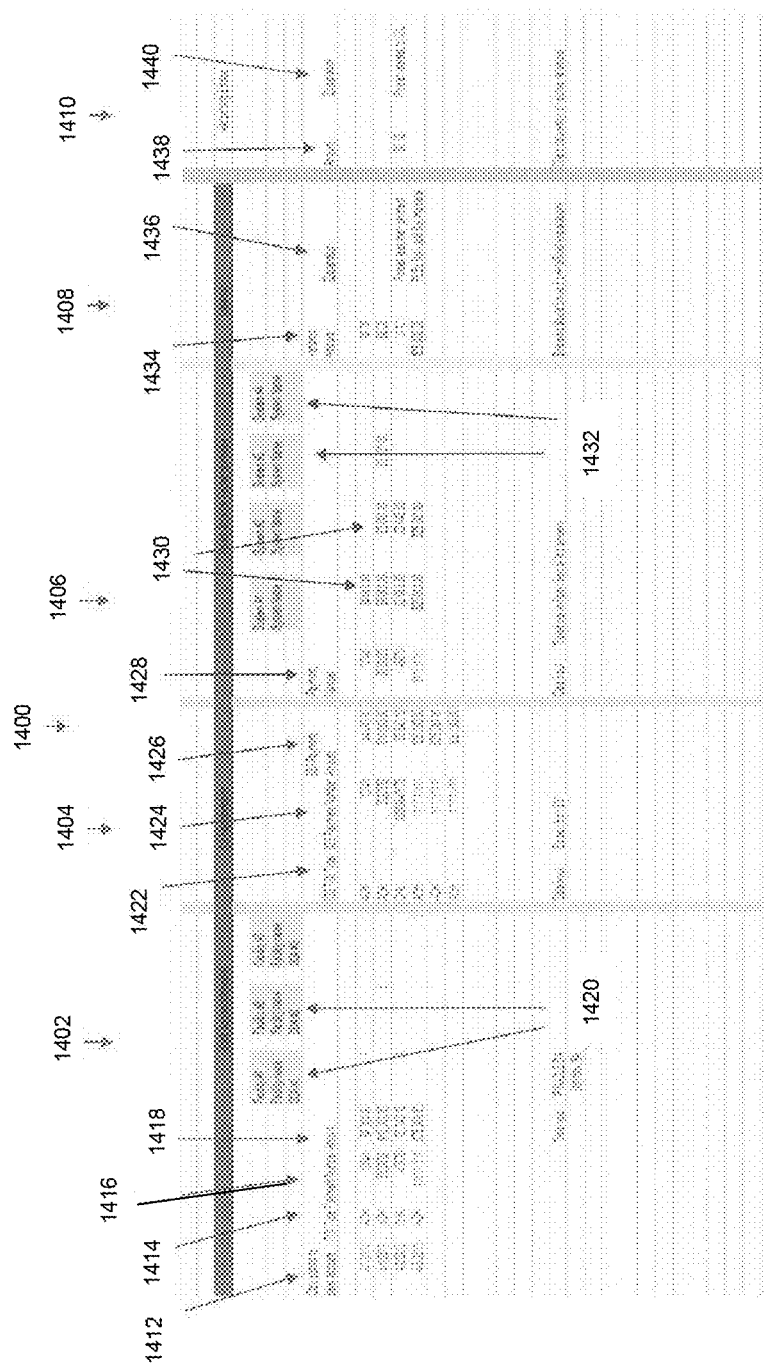
FIGS. 14A and 14B illustrate exemplary graphical user interfaces (GUI) for reconciliation of a healthcare bank account that may be used by the system and method, in accordance with a preferred embodiment of the present disclosure.
Figure 14B:
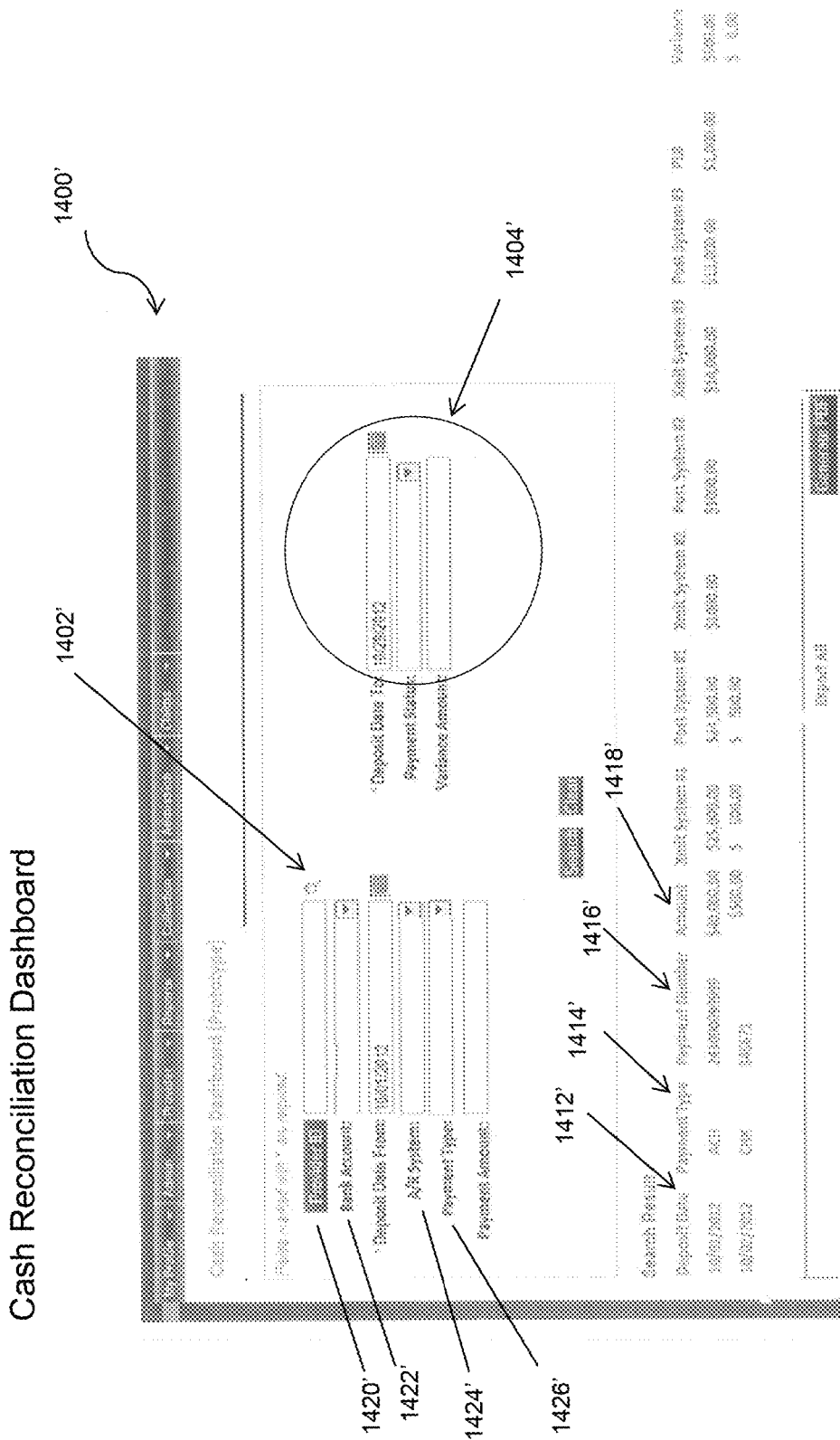
Figure 15:
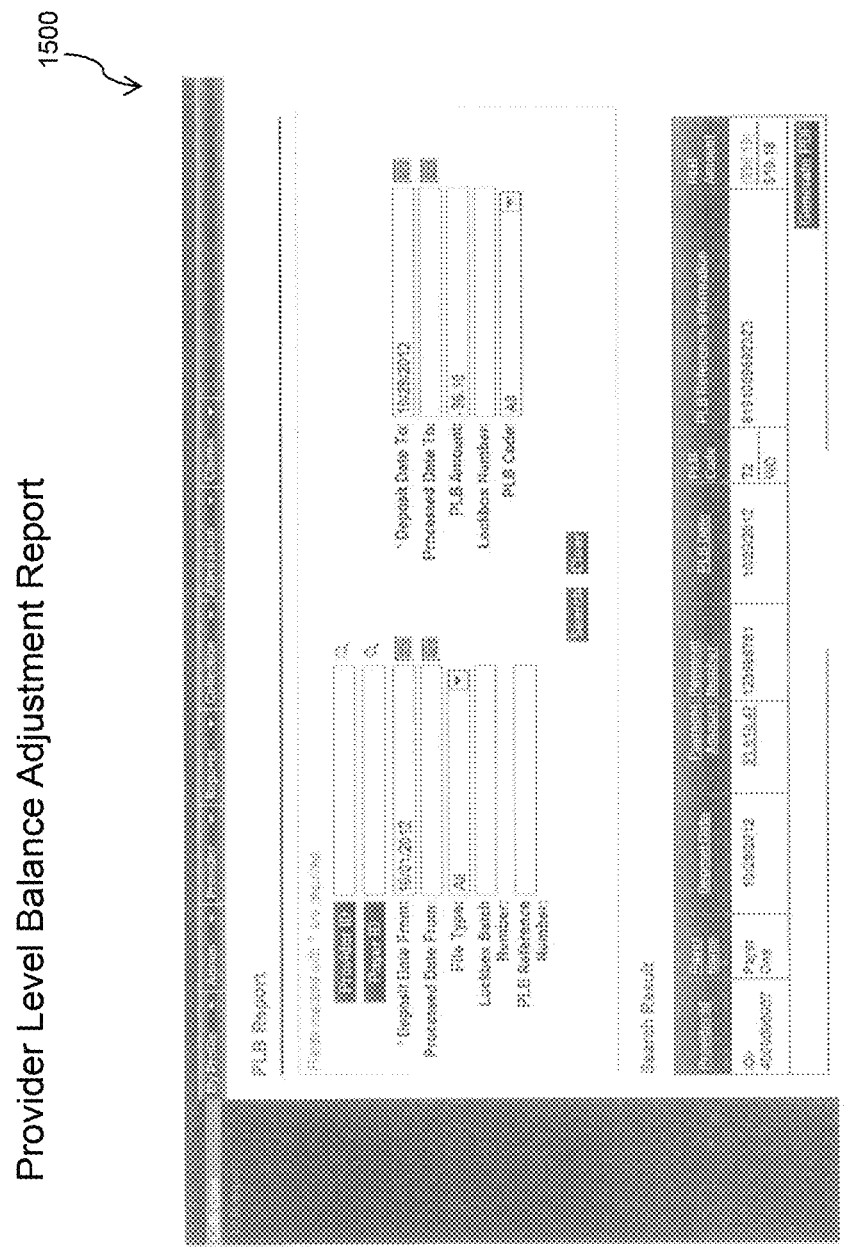
FIG. 15 illustrates an exemplary Provider Level Balance (PLB) Adjustment Report that lists individual transactions included in the exceptions sub-file of the File Split Report, which represent one source of reconciliation variances, that may be produced by the system and method, in accordance with a preferred embodiment of the present disclosure.

In a preferred embodiment, a user interface is provided to enable a user to enter information about a variance, which may include at least one of a transaction to reconcile the variance and information regarding how to reconcile the variance. Exemplary graphical user interfaces (GUI) to perform this are illustrated in FIGS. 14A and 14B, which are referred to as the Cash Reconciliation Dashboards 1400, 1400'. FIG. 14A illustrates a first embodiment of Cash Reconciliation Dashboard GUI 1400, and FIG. 14B illustrates a second embodiment of the GUI 1400'.

In the first embodiment shown in FIG. 14A, the Cash Reconciliation Dashboard 1400 generally includes five groups of columns 1402, 1404, 1406, 1408, 1410. Column 1402 includes bank account information of a healthcare provider. The information in column 1402 may be received from any or all of the data input sources 402, 404, 410, 412, and 414 shown in FIG. 4. Column 1402 is subdivided into columns for transaction information, including the date that a transaction posts to a healthcare provider account 1412, the transaction type 1414, a payment number 1416, and a transaction amount 1418. Each of columns 1412, 1414, 1416, and 1418 are associated with a particular facility 1420 based on an "X" or check indicator.

Column 1404 includes EOB information provided by a payer. In the embodiment shown in FIG. 14A, the Cash Reconciliation Dashboard 1400 displays information received in the format of a Direct 835 file 900; however, other formats are possible. Column 1404 is subdivided into columns for payment information based on the EOB information, including transaction type 1422, payment number 1424, and payment amount 1426.

Column 1406 includes payment amount information that is posted from a patient accounting entity or billing system of the healthcare provider. The information in column 1406 may be received from the data input sources 416 and 424 shown in FIG. 4. In FIG. 14A, column 1406 is subdivided into columns for payment information received for a particular billing system, including payment number 1428, the system name 1432, and an amount 1430 associated with the system name 1432. In addition, the information in column 1406 may be based on accounting entity instead of particular billing system.

Column 1408 displays any variances that are calculated from the information in columns 1402, 1404, and 1406. Column 1408 is subdivided into columns for variance information, including variance amount 1434 and an explanation 1436 for the variance amount 1434. The explanation may be automatically populated with pre-defined explanations that occur as part of the variance calculation or the explanation may be manually input by a user.

Column 1410 displays reconciling entries that are directed to action that is to be taken, or has been taken, by a user. For example, column 1410 is shown as being subdivided into columns for amount 1438 and an explanation 1440 of the reconciling action that was taken. As with the variance explanation, the information in column 1440 may be automatically populated with pre-defined explanations that occur as part of the reconciling action or the explanation may be manually input by a user. Furthermore, the reconciling entries may result in adjustments that are made to the healthcare provider's accounts receivable system and/or general ledger system. Such adjustments may simply be data corrections that are transmitted to the appropriate system; however, other corrections may involve financial transactions that are taken to correct issues.

A smaller or larger number of columns may be provided with any one or all of the columns to provide more or less detail to a transaction.

In the second embodiment shown in FIG. 14B, the Cash Reconciliation Dashboard 1400' generally includes a search field 1402' and input fields 1404' displayed on a portion of the GUI 1400'. These input fields 1404' may be drop-down boxes. Information within the dropdown boxes and other information may be received from any or all of the data input sources 410, 412, and 414 shown in FIG. 4. Another portion of the GUI 1400' may be programmed to display transaction information, including the date that a transaction posts to a healthcare provider account 1412', the transaction type 1414', a payment number 1416', and a transaction amount 1418'. Each of columns 1412', 1414', 1416', and 1418' are associated with a particular Provider ID, Bank Account, A/R System, and/or Payment Type.

In summary, Cash Reconciliation Dashboards 1400, 1400' are provided to compare payment information contained in the multi-system imports, and identify discrepancies by payment number and payment amount. Through GUIs within the Cash Reconciliation Dashboards 1400, 1400', users are able to enter reconciling transactions and comments to resolve variances identified within the Cash Account Reconciliation database 430.

Payment Extract

Following the file splitting process, split 835 sub-files may be transmitted to a file mapping program such as, for example, IBM Message Broker. As shown in FIG. 4, the file mapping program 432 may be part of the Cash Reconciliation Module 428. The file mapping program extracts data from the BPR segment of each newly created 835 sub-file. The 835 payment extract information is then routed to the Cash Account Reconciliation database 430. The 835 payment extract information may be displayed to users in a "835 File Information" column of the Cash Reconciliation Dashboard 1400, 1400'. The 835 payment extract information reflects a match to a check or electronic payment already made in the Reassociation module 408, or it may be matched to check or electronic payment information (ACH) in the "Bank Account Information" of the Cash Reconciliation Dashboard 1400, 1400'. Information about payments made for individual patient services or procedures (which may also be referred to as CLP data) are preferably not passed to the Cash Account Reconciliation database 430.

After resolving variances, users are able to print, convert to a PDF, or export a completed cash account reconciliation report and/or "lock down" the report for the permanent reconciliation archive. In addition, the system may be programmed to record and report automated match rates. These automated match rates may tracked by a client 14 by client 14 basis for auditing and reporting purposes. Furthermore, the system may be programmed to generate a workflow of unreassociated payments. Workflows may be used to research late/missing Direct 835 files 900. The system may also be configured to track and sort reassociated Direct 835 files, unreassociated Direct 835 files, and/or mixed Direct 825 files (includes reassociated and unreassociated transactions). These segmented files may be transmitted to clients 14, as desired.

Furthermore, in preferred embodiments those components listed above may function and be implemented in a single computing device, such as, for example, a server described herein or each component may function and be implemented in separate computing devices, which may or may not be located remotely from each other.

Exemplary Computer System Implementation

As would be appreciated by someone skilled in the relevant art(s) and described below with reference to FIG. 16, part or all of one or more aspects of the methods and system discussed herein may be distributed as an article of manufacture that itself comprises a computer readable medium having computer readable code means embodied thereon.

The computer readable program code means is operable, in conjunction with a computer system, to carry out all or some of the steps to perform the methods or create the system discussed herein. The computer readable medium may be a recordable medium (e.g., hard drives, compact disks, EEPROMs, or memory cards). Any tangible medium known or developed that can store information suitable for use with a computer system may be used. The computer-readable code means is any mechanism for allowing a computer to read instructions and data, such as magnetic variations on a magnetic media or optical characteristic variations on the surface of a compact disk. The medium can be distributed on multiple physical devices (or over multiple networks). For example, one device could be a physical memory media associated with a terminal and another device could be a physical memory media associated with a processing center.

The computer systems and servers described herein each contain a memory that will configure associated processors to implement the methods, steps, and functions disclosed herein. Such methods, steps, and functions may be carried out by processing capability on mobile device, POS terminal, payment processor, acquirer, issuer, or by any combination of the foregoing. The memories may be distributed or local and the processors may be distributed or singular. The memories may be implemented as an electrical, magnetic or optical memory, or any combination of these or other types of storage devices. Moreover, the term "memory" should be construed broadly enough to encompass any information able to be read from or written to an address in the addressable space accessed by an associated processor.

Aspects of the present disclosure shown in the FIGS., or any part(s) or function(s) thereof, may be implemented using hardware, software modules, firmware, tangible computer readable media having instructions stored thereon, or a combination thereof and may be implemented in one or more computer systems or other processing systems.

Figure 16:
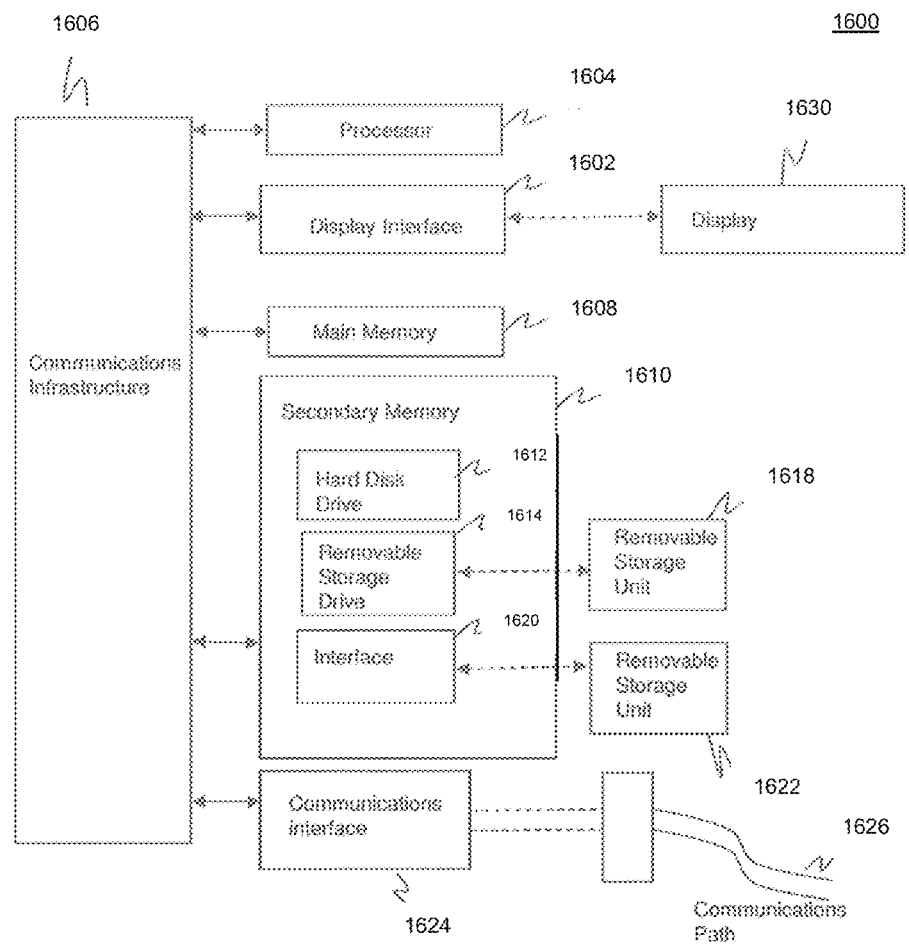
FIG. 16 depicts an example computer system in which embodiments of the present invention may be implemented.

FIG. 16 illustrates an example computer system 1600 in which embodiments of the present disclosure, or portions thereof, may be implemented as computer-readable code. For example, the various aspects of the user interfaces depicted in the FIGS. may be implemented in computer system 1600 using hardware, software, firmware, non-transitory computer readable media having instructions stored thereon, or a combination thereof and may be implemented in one or more computer systems or other processing systems. Hardware, software, or any combination of such may embody any of the modules and components used to implement the network, systems, methods and GUI described above. For example, the client 14, email server 34, transaction server 42, web server 18, application server 20, and/or database server 22 described above with reference to FIGS. 1 and 2 can be implemented using computer system 1600. Also, for example, the respective display devices 228 of clients 14 and the above-listed servers may be implemented as display 1630, which, together with display interface 1602, can be configured to render the GUI depicted in the FIGS.

If programmable logic is used, such logic may execute on a commercially available processing platform or a special purpose device. One of ordinary skill in the art may appreciate that embodiments of the disclosed subject matter can be practiced with various computer system configurations, including multi-core multiprocessor systems, minicomputers, mainframe computers, computers linked or clustered with distributed functions, as well as pervasive or miniature computers that may be embedded into virtually any device. For instance, at least one processor device and a memory may be used to implement the above described embodiments. A processor device may be a single processor, a plurality of processors, or combinations thereof. Processor devices may have one or more processor "cores."

Various embodiments of the present disclosure are described in terms of this example computer system 1600. After reading this description, it will become apparent to a person skilled in the relevant art how to implement the present disclosure using other computer systems and/or computer architectures. Although operations may be described as a sequential process, some of the operations may in fact be performed in parallel, concurrently, and/or in a distributed environment, and with program code stored locally or remotely for access by single or multiprocessor machines. In addition, in some embodiments the order of operations may be rearranged without departing from the spirit of the disclosed subject matter.

The processor device 1604 may be a special purpose or a general purpose processor device. As will be appreciated by persons skilled in the relevant art, processor device 1604 may also be a single processor in a multi-core/multiprocessor system, such system operating alone, or in a cluster of computing devices operating in a cluster or server farm. Processor device 1604 is connected to a communication infrastructure 1606, for example, a bus, message queue, network, or multi-core message-passing scheme.

The computer system 1600 also includes a main memory 1608, for example, random access memory (RAM), and may also include a secondary memory 1610. Secondary memory 1610 may include, for example, a hard disk drive 1612, removable storage drive 1614. Removable storage drive 1614 may comprise a floppy disk drive, a magnetic tape drive, an optical disk drive, a flash memory, or the like.

The removable storage drive 1614 may read from and/or writes to a removable storage unit 1618 in a well-known manner. The removable storage unit 1618 may comprise a floppy disk, magnetic tape, optical disk, Universal Serial Bus ("USB") drive, flash drive, memory stick, etc. which is read by and written to by removable storage drive 1614. As will be appreciated by persons skilled in the relevant art, the removable storage unit 1618 includes a non-transitory computer usable storage medium having stored therein computer software and/or data.

In alternative implementations, the secondary memory 1610 may include other similar means for allowing computer programs or other instructions to be loaded into computer system 1600. Such means may include, for example, a removable storage unit 1622 and an interface 1620. Examples of such means may include a program cartridge and cartridge interface (such as that found in video game devices), a removable memory chip (such as an EPROM, or PROM) and associated socket, and other removable storage units 1622 and interfaces 1620 which allow software and data to be transferred from the removable storage unit 1622 to computer system 1600.

The computer system 1600 may also include a communications interface 1624. In embodiments, the communications interface device 211 described above with reference to FIG. 2 can be implemented with the communications interface 1624. The communications interface 1624 allows software and data to be transferred between the computer system 1600 and external devices. The communications interface 1624 may include a modem, a network interface (such as an Ethernet card), a communications port, a PCM-CIA slot and card, or the like. Software and data transferred via the communications interface 1624 may be in the form of signals, which may be electronic, electromagnetic, optical, or other signals capable of being received by communications interface 1624. These signals may be provided to the communications interface 1624 via a communications path 1626. The communications path 1626 carries signals and may be implemented using wire or cable, fiber optics, a phone line, a cellular/wireless phone link, an RF link or other communications channels.

In this document, the terms 'computer readable storage medium,' 'computer program medium,' 'non-transitory computer readable medium,' and 'computer usable medium' are used to generally refer to tangible and non-transitory media such as removable storage unit 1618, removable storage unit 1622, and a hard disk installed in hard disk drive 1612. Signals carried over the communications path 1626 can also embody the logic described herein. The computer readable storage medium, computer program medium, non-transitory computer readable medium, and computer usable medium can also refer to memories, such as main memory 1608 and secondary memory 1610, which can be memory semiconductors (e.g., DRAMs, etc.). These computer program products are means for providing software to computer system 1600.

Computer programs (also called computer control logic and software) are generally stored in a main memory 1608 and/or secondary memory 1610. The computer programs may also be received via a communications interface 1624. Such computer programs, when executed, enable computer system 1600 to become a specific purpose computer able to implement the present disclosure as discussed herein. In particular, the computer programs, when executed, enable the processor device 1604 to implement the processes of the present disclosure discussed below. Accordingly, such computer programs represent controllers of the computer system 1600. Where the present disclosure is implemented using software, the software may be stored in a computer program product and loaded into the computer system 1600 using the removable storage drive 1614, interface 1620, and hard disk drive 1612, or communications interface 1624.

CONCLUSION

It is to be appreciated that the Detailed Description section, and not the Summary and Abstract sections, is intended to be used to interpret the claims. The Summary and Abstract sections may set forth one or more but not all exemplary embodiments of the present invention as contemplated by the inventor(s), and thus, are not intended to limit the present invention and the appended claims in any way.

Embodiments of the present invention have been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

Although the invention is illustrated and described herein with reference to specific embodiments, the invention is not intended to be limited to the details shown. Rather, various modifications may be made in the details within the scope and range equivalents of the claims and without departing from the spirit and scope of the present invention.

We claim:

1. A system comprising a computing device having a processor, a display, and a non-transitory computer readable medium having instructions stored thereon that, if executed by the processor of the computing device, cause the processor to perform operations for reconciling a healthcare payment account, the operations comprising:
   receiving, by a computing device having a processor, a display, and non-transitory computer readable medium:
      a first electronic file comprising explanation of benefits information from a healthcare payer;
      a second electronic file comprising payment information for a financial account of a healthcare provider; and,
      a third electronic file comprising accounting information from the healthcare provider;
   determining, by a cash account reconciliation module, a first variance, a second variance, and a third variance via a reassociation process, the reassociation process comprising:
      associating at least one provider with at least one payer;
      performing matching via TRN segment and Amount, Trace number, Transaction Date and Amount, and Amount only;
      performing the matching for an entire file and for each transaction; and,
      associating a remittance with a payment for reconciliation;
      wherein the first variance comprises a variance between the first electronic file and the second electronic file, the second variance comprises a variance between the second electronic file and the third electronic file, and the third variance comprises a variance between the first electronic file and the third electronic file;
      wherein the first variance is a discrepancy related to a medical claims payer's explanation of benefits information, the second variance is a discrepancy related to a healthcare provider's banking information, and the third variance is a discrepancy related to a healthcare provider's accounts receivable and general ledger information; and
   displaying by the cash account reconciliation module at least at least one of the first variance, the second variance, and the third variance.

2. The system of claim 1, the operations further comprising displaying at least one search GUI via the computer device programmed to enable a user to search a database and effectuate a manual match of at least one of the first electronic file, the second electronic file, and the third electronic file with at least one of the remittance and the payment.

3. The system of claim 2, the operations further comprising displaying at least one report GUI via the computer device programmed to generate a report based upon the manual match.

4. The system of claim 1, the operations further comprising:
performing a file splitting process by processing at least one of the first electronic file, the second electronic file; and the third electronic file such that at least one of the first electronic file, the second electronic file, and the third electronic file is split into a plurality of separate sub-files based on at least one of an accounting entity and an accounts receivable system;
wherein at least one pre-defined data element within at least one of the first electronic file, the second electronic file, and the third electronic file is used to sort information within at least one of the first electronic file, the second electronic file, and the third electronic file;
wherein the plurality of separate sub-files are subsequently rebalanced to a payment amount on at least one of the first electronic file, the second electronic file, and the third electronic file; and,
wherein if a match is not determined, the at least one pre-defined data element is placed into an exception sub-file.

5. The system of claim 4, the operations further comprising displaying at least one sub-file report GUI via the computer device programmed to generate a report based upon the exception sub-file.

6. The system of claim 5, wherein the at least one sub-file report GUI is programmed to generate a MB Adjustment Report.

7. The system of claim 4, wherein the sorting is based on client-specific business rules.

8. The system of claim 4, the operations further comprising displaying at least one File Split Report GUI via the computer device programmed to generate a report based upon the plurality of separate split files.

9. The system of claim 4, the operations further comprising mapping at least some of the plurality of separate sub-files to display payment extraction information via at least one GUI.

10. The system of claim 9, wherein the mapping is performed through the cash account reconciliation module.

11. The system of claim 4, wherein at least one of the first electronic file, the second electronic file, and the third electronic file is received by both a reassociation module and a file splitting module to match the explanation of benefits information with payment information before determining the first variance, the second variance, and the third variance, wherein the reassociation module is programmed to perform the reassociation process and the file splitting module is programmed to perform the file splitting process.

12. The system of claim 11, wherein the file splitting process is used, in part, to identify how files should be split after the reassociation with the payment information is completed.

13. The system of claim 4, the operations further comprising rebalancing the plurality of separate sub-files such that totals of each of the plurality of separate sub-files when taken together equal a total payment amount of at least one of the first electronic file, the second electronic file, and the third electronic file.

14. The system of claim 13, wherein the plurality of rebalanced separate files is a complete payment file.

15. The system of claim 1, the operations further comprising displaying at least one Cash Reconciliation Dashboard programmed to enable a user to enter information about at least one of the first variance, the second variance, and the third variance to reconcile at least one of the first variance, the second variance, and the third variance.

16. The system of claim 1, wherein the first electronic file further comprises an explanation for how payment for a medical claim was calculated by the healthcare payer and the second electronic file further comprises at least one of check payment information, ACH information, and EFT information.

17. The system of claim 1, wherein at least one of the first electronic file, the second electronic file, and the third electronic file is validated, reformatted, and transmitted to an application server before determining the first variance, the second variance, and the third variance.

18. The system of claim 1, wherein at least one of the first electronic file, the second electronic file, and the third electronic file is transmitted to at least one of a reporting module and a database server after being reformatted.

19. The system of claim 1, wherein the associating at least one provider with at least one payer is based in part on an ID qualifier.

20. The system of claim 1, wherein the accounting information from the healthcare provider comprises payment posting data from at least one of an accounts receivable system of the healthcare provider and a general ledger system of the healthcare provider.

* * * * *